US012569185B2

(12) United States Patent
Muhammed et al.

(10) Patent No.: US 12,569,185 B2
(45) Date of Patent: Mar. 10, 2026

(54) SYSTEMS AND METHODS FOR SUBJECT ASSESSMENT

(71) Applicant: Kneu Health Limited, London (GB)

(72) Inventors: Kinan Muhammed, Oxford (GB);
Caroline Cake, Walton-on-Thames
(GB); Siddharth Arora, Oxford (GB);
Michele Tao-Ming Hu, Oxford (GB)

(73) Assignee: KNEU HEALTH LIMITED, London
(GB)

( * ) Notice: Subject to any disclaimer, the term of this
patent is extended or adjusted under 35
U.S.C. 154(b) by 0 days.

(21) Appl. No.: 18/815,353

(22) Filed: Aug. 26, 2024

(65) Prior Publication Data

US 2025/0099019 A1     Mar. 27, 2025

Related U.S. Application Data

(60) Provisional application No. 63/585,049, filed on Sep.
25, 2023.

(51) Int. Cl.
*A61B 5/00* (2006.01)
*A61B 5/11* (2006.01)
*A61B 5/16* (2006.01)
*G16H 10/20* (2018.01)
*G16H 10/60* (2018.01)
(Continued)

(52) U.S. Cl.
CPC .......... *A61B 5/4088* (2013.01); *A61B 5/0073*
(2013.01); *A61B 5/1101* (2013.01); *A61B
5/112* (2013.01); *A61B 5/162* (2013.01); *A61B
5/4023* (2013.01); *A61B 5/4812* (2013.01);
*A61B 5/7275* (2013.01); *G16H 10/20*

(2018.01); *G16H 10/60* (2018.01); *G16H
20/10* (2018.01); *G16H 50/20* (2018.01);
*G16H 50/30* (2018.01);
(Continued)

(58) Field of Classification Search
CPC ........... A61B 5/4088; A61B 5/11; A61B 5/40
See application file for complete search history.

(56) References Cited

U.S. PATENT DOCUMENTS

2020/0261013 A1*   8/2020   Ben-Oren .............. G16H 20/70
2022/0199245 A1*   6/2022   Wipperman ........... A61B 5/291

OTHER PUBLICATIONS

Greffard et al, "Motor Score of the Unified Parkinson Disease
Rating Scale as a Good Predictor of Lewy Body-Associated Neuronal
Loss in the Substantia Nigra", American Medical Association, 2006
(Year: 2006).*

(Continued)

*Primary Examiner* — James M Kish
*Assistant Examiner* — Jessica L Mullins
(74) *Attorney, Agent, or Firm* — Wilson Sonsini Goodrich
& Rosati

(57) ABSTRACT

The present disclosure provides systems and methods for
performing a clinical assessment of a neurological disease,
disorder, or condition. In an aspect, a system may comprise
sensors, which sensors are configured to acquire sensor data
of the subject over a period of time; and which mobile
electronic device, comprises: an electronic display; a wire-
less transceiver; and one or more computer processors
configured to (i) receive the sensor data from the sensors, (ii)
process the sensor data or features extracted therefrom using
a trained algorithm to generate an output indicative of a state
of a neurological disease, disorder, or condition of the
subject, and (iii) based at least in part on the generated
output, perform a clinical assessment on the subject.

24 Claims, 13 Drawing Sheets

(51) Int. Cl.
 *G16H 20/10*     (2018.01)
 *G16H 50/20*     (2018.01)
 *G16H 50/30*     (2018.01)
(52) U.S. Cl.
 CPC . *A61B 2560/045* (2013.01); *A61B 2562/0204* (2013.01); *A61B 2562/0219* (2013.01)

(56) References Cited

OTHER PUBLICATIONS

Arnaldi, Dario et al., Dopaminergic imaging and clinical predictors for phenoconversion of REM sleep behaviour disorder. Brain. 144(1):278-287 (2021).

Arora, Siddharth et al., Smartphone motor testing to distinguish idiopathic REM sleep behavior disorder, controls, and PD. Neurology. 91(16):e1528-e1538 (2018).

Höglinger, Günter U. et al., Towards a Biological Definition of Parkinson's Disease. Preprints.org, Concept Paper. 22 pages (2023).

Jackson, Holly et al., Hoehn and Yahr Stage and Striatal Dat-SPECT Uptake Are Predictors of Parkinson's Disease Motor Progression. Front Neurosci. 15:765765, pp. 1-10 (2021).

Lo, Christine et al., A composite clinical motor score as a comprehensive and sensitive outcome measure for Parkinson's disease. J Neurol Neurosurg Psychiatry. 93(6):617-624 (2022).

Marek, Kenneth et al., The Parkinson's progression markers initiative (PPMI)—establishing a PD biomarker cohort. Annals of Clinical and Translational Neurology. 5(12):1460-1477 (2018).

Schrag, Anette et al., Clinical variables and biomarkers in prediction of cognitive impairment in patients with newly diagnosed Parkinson's disease: a cohort study. Lancet Neurol. 16(1):66-75 (2017).

Simuni, Tanya et al., A Biological Definition and Integrated Staging System of Neuronal alpha- Synuclein Disease. The Michael J. Fox Foundation for Parkinson's Research. 19 pages (2023). Available at https://www.michaeljfox.org/sites/default/files/media/document/NSD-ISS%20Manuscript%20for%20Public%20Comment%20062123_1_0.pdf.

Arora, Siddharth. et al. Detecting and monitoring the symptoms of Parkinson's disease using smartphones: A pilot study. Parkinsonism & related disorders 21(6):650-653 (2015).

Arora, Siddharth. et al. Smartphone speech testing for symptom assessment in rapid eye movement sleep behavior disorder and Parkinson's disease. IEEE Access 9:44813-44824 (2021).

Neu Health. Internet Archive, Aug. 7, 2023; [retrieved on Feb. 10, 2025]. Available at URL:https://web.archive.org/web/20230807234747/https://neu.health/ pp. 1-5.

PCT/IB2024/000428 International Search Report and Written Opinion dated Nov. 11, 2024.

\* cited by examiner

Voice

Time: 1 min

0/7 Complete

Instructions: Take a deep breath and say "aaaah" for as long and steadily as you can.

Requirements: A quiet space with no background noise.

Start

Balance
Time: 1 min
1/7 Complete
Instructions: Place the phone in your pocket and remain standing still for 20 seconds.
Requirements: Stand with feet shoulder width apart and place the phone vertically in a pocket.
Start
FIG. 1B

Walking
Time: 1 min
2/7 Complete
Instructions: Place the phone in your pocket, walk forward in a straight line, turn around and walk back again, repeat until the exercise ends.
Requirements: Space to walk safely and a pocket to hold the phone vertically.
Start
FIG. 1C

Tapping

3/7 Complete

Time: 1 min

Instructions: Tap the buttons alternating between your middle and index fingers on your LEFT hand first. Keep a regular and steady pace.

Requirements: Place the phone on a flat surface with a clean screen.

Start

Reaction Time
4/7 Complete
Time: 1 min
Instructions: A button will appear on the screen. Press the button as soon as it appears. Keep pressing whilst it is on the screen. Lift your finger off the button as soon as it disappears.
Requirements: Place the phone on a flat surface with a clean screen.
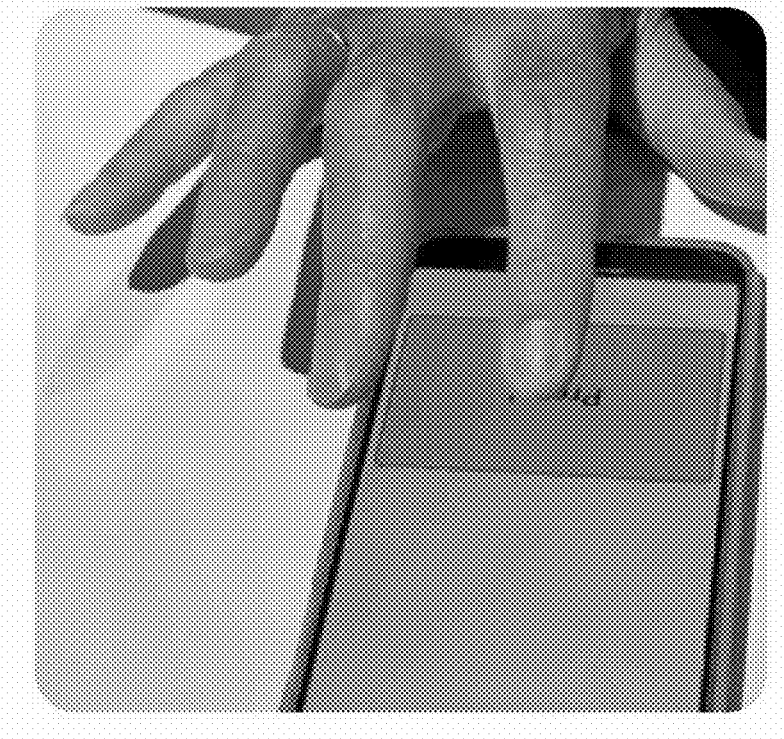
Start
FIG. 1F

Rest Tremor

Time: 1 min

5/7 Complete

Instructions: Hold the phone in your LEFT hand and place the back of your hand on a flat hard surface. Close your eyes and count backwards from 100.

Requirements: Rest your hand on a flat surface, hold the phone flat in your hand.

Start

Postural Tremor

6/7 Complete

Time: 1 min

Instructions: Hold the phone in your LEFT hand with your arm outstretched in front of you. Close your eyes and count backwards from 100.

Requirements: Hold your arm straight out in front of you, hold the phone flat in your hand.

Start

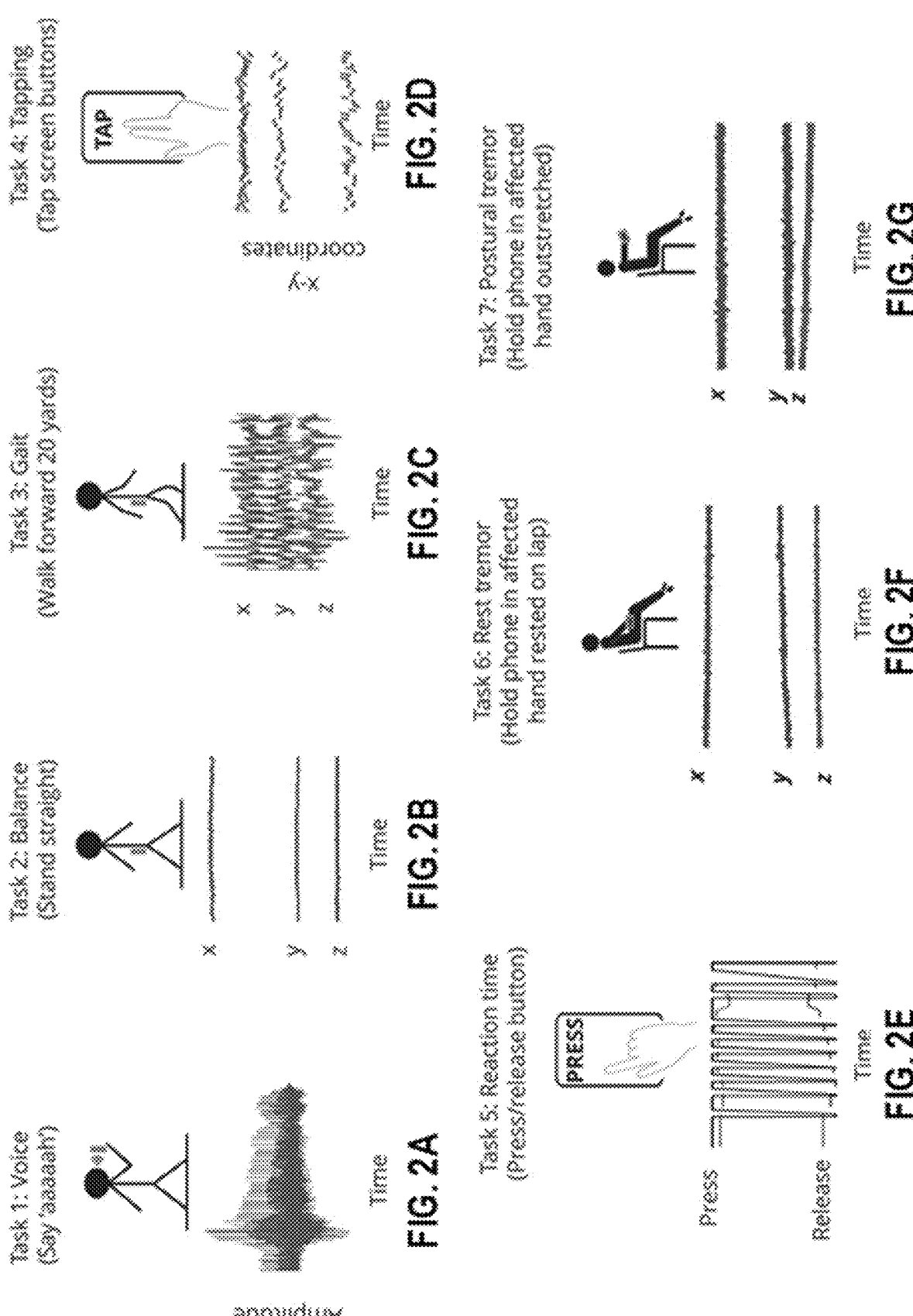

SYSTEMS AND METHODS FOR SUBJECT ASSESSMENT

CROSS-REFERENCE

This application claims the benefit of U.S. Provisional Application No. 63/585,049, filed Sep. 25, 2023, which is incorporated by reference herein in its entirety.

BACKGROUND

Neurological diseases and disorders encompass a wide range of conditions affecting the brain, spinal cord, and nerves. Timely detection and diagnosis of such diseases, disorders, and conditions is crucial for effective treatment and management. Traditional methods of diagnosis often involve complex and expensive tests, which may not be accessible or affordable for many individuals. Moreover, the symptoms of neurological disorders can be subtle and easily overlooked, leading to delayed diagnosis, misdiagnosis, or potential complications.

SUMMARY

Many neurological disorders, for example Parkinson's disease (PD), are marked by a loss of motor function. In the U.S. nearly 90,000 people are diagnosed with Parkinson's disease (PD) each year, and more than 10 million people are living with PD worldwide. Accurate and early diagnosis of Parkinson's disease using biologically-driven criteria is crucial for patient prognosis, particularly when considering the potential differential diagnoses (e.g., essential tremor, atypical parkinsonism, dementia with Lewy bodies, multiple system atrophy, progressive supranuclear palsy, corticobasal degeneration, or prodromal stage Parkinson's disease including rapid eye movement sleep behavior disorder) and the progressive loss of motor and non-motor function associated with the disease. By utilizing these criteria, healthcare professionals can identify the condition at an earlier stage, enabling prompt initiation of appropriate treatment interventions. This early intervention has the potential to slow down disease progression and preserve the patient's motor and non-motor function to a certain extent. Moreover, biologically-driven criteria aid in distinguishing Parkinson's disease from other conditions with similar symptoms, ensuring that patients receive tailored and targeted therapies specific to their diagnosed condition.

Diagnosis of Parkinson's disease using biologically-driven criteria may require showing loss of dopamine neurons (e.g., dopaminergic neurons) in the basal ganglia. This loss may be clinically assessed through radiological brain imaging techniques (e.g., a Dopamine Active Transporter tomography scan, DaTscan) or through sleep studies (e.g., polysomnography). However, these tests may not be accessible or affordable for many individuals. For example, a DaTscan may cost about $3,000 to $5,000, require a testing time of about 3 to 6 hours, and a wait time of several months. Therefore, there remains a need for alternatives to DaTscan testing that provide lower cost and complexity for increased accessibility of clinically actionable tools for assessing or diagnosing Parkinson's disease (e.g., early-stage Parkinson's disease).

Recognized herein is the need for affordable and accessible systems and methods of clinical assessment of a neurological disease, disorder, or condition in a subject. Using a mobile electronic device that monitors, collects, and/or records motor and non-motor function data, subjects may be assessed during the performance of a motor task (e.g., at the subject's home, instead of a clinical setting such as a hospital) over a period of time to predict a likelihood of the subject having a state of the neurological disease, disorder, or condition (e.g., Parkinson's disease, essential tremor, atypical parkinsonism, dementia with Lewy bodies, multiple system atrophy, progressive supranuclear palsy, corticobasal degeneration, or prodromal stage Parkinson's disease including rapid eye movement (REM) sleep behavior disorder).

The present disclosure provides systems and methods that may advantageously collect and analyze sensor data over a period of time to accurately and non-invasively predict a likelihood of the subject having a state of a neurological disease, disorder, or condition.

In an aspect, the present disclosure provides a system for performing a clinical assessment of a neurological disease, disorder, or condition on a subject, comprising: one or more sensors, wherein the one or more sensors are configured to acquire sensor data of the subject over a period of time; and one or more computer processors operatively coupled to the one or more sensors, wherein the one or more computer processors are programmed to: (i) receive the sensor data from the one or more sensors, (ii) process the sensor data or features extracted therefrom using a trained machine learning algorithm to generate an output indicative of the state of the neurological disease, disorder, or condition of the subject, and (iii) based at least in part on the generated output, perform the clinical assessment on the subject, wherein the clinical assessment comprises a clinical examination, a clinical questionnaire, a radiological brain imaging test, or a radiological brain imaging test or a polysomnography (PSG) test.

In some embodiments, (ii) further comprises (a) processing the sensor data to determine motor function scores or cognitive function scores, and (b) processing the motor function scores or cognitive function scores to generate the output.

In some embodiments, the one or more computer processors are programmed to further provide a treatment to the subject based at least in part on the clinical assessment.

In some embodiments, the system further comprises a mobile electronic device. In some embodiments, the mobile electronic device comprises an electronic display. In some embodiments, the mobile electronic device comprises a wireless transceiver.

In some embodiments, the one or more sensors comprise a member selected from the group consisting of an accelerometer, a touch screen sensor, a video sensor, an audio sensor, and a gyroscope sensor. In some embodiments, the accelerometer comprises a triaxial accelerometer. In some embodiments, the touch screen sensor comprises a resistive touch sensor. In some embodiments, the touch screen sensor comprises a capacitive touch sensor. In some embodiments, the touch screen sensor comprises a surface acoustic wave sensor. In some embodiments, the video sensor comprises a camera. In some embodiments, the audio sensor comprises a microphone.

In some embodiments, the sensor data comprise data obtained during the performance of a motor task or a cognitive task by the subject. In some embodiments, the motor task or the cognitive task is a member selected from the group consisting of tasks measuring vocalization, balance, gait, tapping, reaction time, resting tremor, and postural tremor.

In some embodiments, the sensor data comprise inertial measurement units (IMUs). In some embodiments, the sensor data comprise event times. In some embodiments, the sensor data comprise coordinates of the electronic display. In some embodiments, the sensor data comprise audio recordings. In some embodiments, the sensor data comprise digital images. In some embodiments, the sensor data comprise video recordings.

In some embodiments, (ii) further comprises processing patient reported outcome measure (PROM) data, medication-specific data, or data from a behavioral test of cognitive function, using the trained machine learning algorithm. In some embodiments, (ii) further comprises processing at least one of the sensor data, the PROM data, or the data from the behavioral test of cognitive function, to determine motor function scores or cognitive function scores; and processing the motor function scores or cognitive function scores to generate the output. In some embodiments, the PROM data comprise quality of life, pain, fatigue, patient function including activities of daily living, clinical events such as falls and hospital admissions, or symptom severity data. In some embodiments, the behavioral test of cognitive function comprises a Montreal Cognitive Assessment (MoCA) or a digital test of processing speed, working memory, an Addenbrookes Cognitive Examination (ACE-III), or a digital test of processing speed, working memory, short-term episodic memory, long-term episodic memory, or executive function. In some embodiments, the medication-specific data comprises medication specific to the treatment of the neurological disease, disorder, or condition, such as type, dose, frequency, timing, or side effects.

In some embodiments, the trained machine learning algorithm comprises a machine learning classifier configured to process the sensor data or the features extracted therefrom, to generate the output. In some embodiments, the machine learning classifier is selected from the group consisting of a support vector machine (SVM), a naïve Bayes classification, a random forest, a neural network, a deep neural network (DNN), a recurrent neural network (RNN), a deep RNN, a long short-term memory (LSTM) recurrent neural network (RNN), and a gated recurrent unit (GRU) recurrent neural network (RNN).

In some embodiments, the neurological disease, disorder, or condition comprises a disease, disorder, or condition selected from the group consisting of Parkinson's disease, dementia with Lewy bodies, multiple system atrophy, prodromal stage Parkinson's disease, progressive supranuclear palsy (PSP), corticobasal degeneration (CBD), parasomnia, REM Sleep Behavior Disorder (RBD), Parkinson's dementia, and dementia.

In some embodiments, the neurological disease, disorder, or condition comprises Parkinson's disease. In some embodiments, the neurological disease, disorder, or condition comprises dementia with Lewy bodies. In some embodiments, the neurological disease, disorder, or condition comprises multiple system atrophy. In some embodiments, the neurological disease, disorder, or condition comprises prodromal stage Parkinson's disease. In some embodiments, the neurological disease, disorder, or condition comprises progressive supranuclear palsy (PSP). In some embodiments, the neurological disease, disorder, or condition comprises corticobasal degeneration (CBD). In some embodiments, the neurological disease, disorder, or condition comprises a parasomnia. In some embodiments, the neurological disease, disorder, or condition comprises REM Sleep Behavior Disorder (RBD). In some embodiments, the neurological disease, disorder, or condition comprises Parkinson's dementia. In some embodiments, the neurological disease, disorder, or condition comprises dementia. In some embodiments, the clinical assessment comprises the radiological brain imaging test.

In some embodiments, the radiological brain imaging test comprises determining dopamine neuron loss.

In some embodiments, the radiological brain imaging test comprises determining dopamine neuron loss in a brain area.

In some embodiments, the radiological brain imaging test comprises a generating a visualization of the dopamine system in a brain area. In some embodiments, the brain area comprises a member selected from the group consisting of the striatum, the putamen, and the caudate nucleus.

In some embodiments, the radiological brain imaging test comprises a Dopamine Active Transporter tomography scan (DaTscan). In some embodiments, the DaTscan comprises a Dopamine Active Transporter ioflupane (123I) single photon emission tomography scan.

In some embodiments, the clinical assessment comprises the polysomnography (PSG) test.

In some embodiments, the PSG test comprises a sleep study.

In some embodiments, the PSG test is used to detect a presence or an absence of rapid eye movement (REM) sleep behavior disorder (RBD) in the subject.

In some embodiments, the generated output indicates a severity of motor impairment in the subject.

In some embodiments, the generated output correlates with a result of the clinical assessment.

In some embodiments, the generated output correlates with DaTscan tracer uptake.

In some embodiments, the generated output correlates with a DaTscan striatal binding ratio.

In some embodiments, the generated output is used to classify the subject as having a pre-determined outcome of the clinical assessment or likely to have a pre-determined outcome of the clinical assessment.

In some embodiments, the generated output comprises a predicted risk or likelihood of the subject having a pre-determined outcome of the clinical assessment.

In some embodiments, the generated output comprises a predicted severity of the neurological disease, disorder, or condition in the subject.

In some embodiments, the generated output comprises an indication of whether the subject is likely to benefit from enrollment into a clinical trial.

In some embodiments, the generated output comprises an indication of whether the subject is likely to benefit from initiation or alteration of medications or therapies.

In some embodiments, the generated output provides sufficient evidence to detect the neurological disease, disorder, or condition in the subject.

In some embodiments, the generated output comprises an estimated composite clinical motor score (CMS), an estimated clinical cognitive score (CCS), an estimated UPDRS total, or a UPDRS-III score. In some embodiments, the CMS comprises components of a Movement Disorders Society-Unified Parkinson's Disease Rating Scale (MDS-UPDRS) III motor examination score, a Purdue Pegboard Test score, or a Timed Up and Go Test score. In some embodiments, the estimated CMS has a mean error of less than about 10 points, less than about 7 points, or less than about 5 points.

In some embodiments, the generated output comprises a set of salient features, wherein the set of salient features is less than about 100 salient features of the sensor data, less than about 75 salient features of the sensor data, less than about 55 features of the sensor data, or less than about 50 salient features of the sensor data. In some embodiments, the set of salient features are the most salient features of the sensor data.

In some embodiments, the generated output has a non-linear correlation with an outcome of the clinical assessment.

In some embodiments, the generated output has a negative correlation with an outcome of the clinical assessment.

In some embodiments, the generated output has a correlation coefficient of less than about negative 0.5 with an outcome of the clinical assessment.

In some embodiments, (ii) further comprises processing patient reported outcome measure (PROM) data or data from a behavioral test of cognitive function, using the trained machine learning algorithm. In some embodiments, (ii) further comprises processing at least one of the sensor data, the PROM data, or the data from the behavioral test of cognitive function, to determine a motor function score; and processing the motor function score to generate the output. In some embodiments, the PROM data comprise quality of life, pain, or fatigue data. In some embodiments, the behavioral test of cognitive function comprises a Montreal Cognitive Assessment (MoCA) or a digital test of processing speed, working memory, or executive function.

In another aspect, the present disclosure provides a method of performing a clinical assessment of a neurological disease, disorder, or condition on a subject, comprising: (i) receiving sensor data from one or more sensors; (ii) using one or more programmed computer processors to process the sensor data or features extracted therefrom, using a trained machine-learning algorithm to generate an output indicative of the state of the neurological disease, disorder, or condition of the subject; and (iii) based at least in part on the generated output, performing the clinical assessment on the subject, wherein the clinical assessment comprises a clinical examination, a clinical questionnaire, a radiological brain imaging test or a polysomnography test.

In some embodiments, (ii) further comprises (a) processing the sensor data to determine motor function scores or cognitive function scores, and (b) processing the motor function scores or cognitive function scores to generate the output.

In some embodiments, the one or more computer processors are programmed to further provide a treatment to the subject based at least in part on the clinical assessment.

In some embodiments, the method further comprises using a mobile electronic device to record the sensor data. In some embodiments, the mobile electronic device comprises an electronic display. In some embodiments, the mobile electronic device comprises a wireless transceiver.

In some embodiments, the one or more sensors comprises a member selected from the group consisting of an accelerometer, a touch screen sensor, a video sensor, an audio sensor, and a gyroscope sensor. In some embodiments, the accelerometer comprises a triaxial accelerometer. In some embodiments, the touch screen sensor comprises a resistive touch sensor. In some embodiments, the touch screen sensor comprises a capacitive touch sensor. In some embodiments, the touch screen sensor comprises a surface acoustic wave sensor. In some embodiments, the video sensor comprises a camera. In some embodiments, the audio sensor comprises a microphone.

In some embodiments, the sensor data comprise data obtained during the performance of a motor task or a cognitive task by the subject. In some embodiments, the motor task or the cognitive task is a member selected from the group consisting of tasks measuring vocalization, balance, gait, tapping, reaction time, resting tremor, and postural tremor.

In some embodiments, the sensor data comprise inertial measurement units (IMUs). In some embodiments, the sensor data comprise event times. In some embodiments, the sensor data comprise coordinates of the electronic display. In some embodiments, the sensor data comprise audio recordings. In some embodiments, the sensor data comprise digital images. In some embodiments, the sensor data comprise video recordings.

In some embodiments, (ii) further comprises processing patient reported outcome measure (PROM) data, medication-specific data, or data from a behavioral test of cognitive function, using the trained machine learning algorithm. In some embodiments, (ii) further comprises processing at least one of the sensor data, the PROM data, or the data from the behavioral test of cognitive function, to determine motor function scores or cognitive function scores; and processing the motor function scores or cognitive function scores to generate the output. In some embodiments, the PROM data comprise quality of life, pain, fatigue, patient function including activities of daily living, clinical events such as falls and hospital admissions, or symptom severity data. In some embodiments, the behavioral test of cognitive function comprises a Montreal Cognitive Assessment (MoCA) or a digital test of processing speed, working memory, an Addenbrookes Cognitive Examination (ACE-III), or a digital test of processing speed, working memory, short-term episodic memory, long-term episodic memory, or executive function. In some embodiments, the medication-specific data comprises medication specific to the treatment of the neurological disease, disorder, or condition, such as type, dose, frequency, timing, or side effects.

In some embodiments, the trained machine learning algorithm comprises a machine learning classifier configured to process the sensor data or the features extracted therefrom, to generate the output. In some embodiments, the machine learning classifier is selected from the group consisting of a support vector machine (SVM), a naïve Bayes classification, a random forest, a neural network, a deep neural network (DNN), a recurrent neural network (RNN), a deep RNN, a long short-term memory (LSTM) recurrent neural network (RNN), and a gated recurrent unit (GRU) recurrent neural network (RNN).

In some embodiments, the neurological disease, disorder, or condition comprises a disease, disorder, or condition selected from the group consisting of Parkinson's disease, dementia with Lewy bodies, multiple system atrophy, prodromal stage Parkinson's disease, progressive supranuclear palsy (PSP), corticobasal degeneration (CBD), parasomnia, REM Sleep Behavior Disorder (RBD), Parkinson's dementia, and dementia.

In some embodiments, the neurological disease, disorder, or condition comprises Parkinson's disease. In some embodiments, the neurological disease, disorder, or condition comprises dementia with Lewy bodies. In some embodiments, the neurological disease, disorder, or condition comprises multiple system atrophy. In some embodiments, the neurological disease, disorder, or condition comprises prodromal stage Parkinson's disease. In some embodiments, the neurological disease, disorder, or condition comprises progressive supranuclear palsy (PSP). In some embodiments, the neurological disease, disorder, or condition comprises corticobasal degeneration (CBD). In some embodiments, the neurological disease, disorder, or condition comprises a parasomnia. In some embodiments, the neurological disease, disorder, or condition comprises REM Sleep Behavior Disorder (RBD). In some embodiments, the neurological disease, disorder, or condition comprises Parkinson's dementia. In some embodiments, the neurological disease, disorder, or condition comprises dementia. In some embodiments, the clinical assessment comprises the radiological brain imaging test.

In some embodiments, the radiological brain imaging test comprises determining dopamine neuron loss.

In some embodiments, the radiological brain imaging test comprises determining dopamine neuron loss in a brain area.

In some embodiments, the radiological brain imaging test comprises generating a visualization of the dopamine system in a brain area. In some embodiments, the brain area comprises a member selected from the group consisting of the striatum, the putamen, and the caudate nucleus.

In some embodiments, the radiological brain imaging test comprises a Dopamine Active Transporter tomography scan (DaTscan). In some embodiments, the DaTscan comprises a Dopamine Active Transporter ioflupane (123I) single photon emission tomography scan.

In some embodiments, the clinical assessment comprises the polysomnography (PSG) test.

In some embodiments, the PSG test comprises a sleep study.

In some embodiments, the PSG test is used to detect a presence or an absence of rapid eye movement (REM) sleep behavior disorder (RBD) in the subject.

In some embodiments, the generated output indicates a severity of motor impairment in the subject.

In some embodiments, the generated output correlates with a result of the clinical assessment.

In some embodiments, the generated output correlates with DaTscan tracer uptake.

In some embodiments, the generated output correlates with a DaTscan striatal binding ratio.

In some embodiments, the generated output is used to classify the subject as having a pre-determined outcome of the clinical assessment or likely to have a pre-determined outcome of the clinical assessment.

In some embodiments, the generated output comprises a predicted the risk or likelihood probability of the subject having a pre-determined outcome of the clinical assessment.

In some embodiments, the generated output comprises a predicted severity of the neurological disease, disorder, or condition in the subject.

In some embodiments, the generated output comprises an indication of whether the subject is likely to benefit from enrollment into a clinical trial.

In some embodiments, the generated output comprises an indication of whether the subject is likely to benefit from initiation or alteration of medications or therapies.

In some embodiments, the generated output provides sufficient evidence to detect the neurological disease, disorder, or condition in the subject.

In some embodiments, the generated output comprises an estimated composite clinical motor score (CMS), an estimated clinical cognitive score (CCS), an estimated UPDRS total, or a UPDRS-III score. In some embodiments, the CMS comprises components of a Movement Disorders Society-Unified Parkinson's Disease Rating Scale (MDS-UPDRS) III motor examination score, a Purdue Pegboard Test score, or a Timed Up and Go Test score. In some embodiments, the estimated CMS has a mean error of less than about 10 points, less than about 7 points, or less than about 5 points.

In some embodiments, the generated output comprises a set of salient features, wherein the set of salient features is less than about 100 salient features of the sensor data, less than about 75 salient features of the sensor data, less than about 55 features of the sensor data, or less than about 50 salient features of the sensor data. In some embodiments, the salient features are the most salient features of the sensor data.

In some embodiments, the generated output has a non-linear correlation with an outcome of the clinical assessment.

In some embodiments, the generated output has a negative correlation with an outcome of the clinical assessment.

In some embodiments, the generated output has a correlation coefficient of less than about negative 0.5 with an outcome of the clinical assessment.

In another aspect, the present disclosure provides a system for performing a clinical assessment of a neurological disease, disorder, or condition on a subject, comprising: a communications interface in network communication with a mobile electronic device of a user, wherein the communication interface receives from the mobile electronic device sensor data collected from a subject using one or more sensors or features extracted therefrom; one or more computer processors operatively coupled to the communications interface, wherein the one or more computer processors are individually or collectively programmed to (i) receive the sensor data or features extracted therefrom from the communications interface, (ii) use a trained machine learning algorithm to process the sensor data or features extracted therefrom, to generate an output indicative of a state of the neurological disease, disorder, or condition, and (iii) direct the output to the mobile electronic device over the network.

In some embodiments, the trained machine learning algorithm comprises a machine learning-based classifier configured to process the motor function data to generate the output of indicative of the state of the neurological disease, disorder, or condition in the subject.

In some embodiments, the neurological disease, disorder, or condition is Parkinson's disease.

In another aspect, the present disclosure provides a system for performing a clinical assessment of Parkinson's disease on a subject, comprising: one or more sensors, wherein the one or more sensors are configured to acquire sensor data of the subject over a period of time; and one or more computer processors operatively coupled to the one or more sensors, wherein the one or more computer processors are programmed to: (i) receive the sensor data from the one or more sensors, (ii) process the sensor data or features extracted therefrom using a trained machine learning algorithm to generate an output indicative of the state of the neurological disease, disorder, or condition of the subject, and (iii) based at least in part on the generated output, perform the clinical assessment on the subject, wherein the clinical assessment comprises a clinical examination, a clinical questionnaire, a radiological brain imaging test, or a polysomnography test.

In some embodiments, the one or more computer processors are part of an electronic device separate from the one or more sensors. In some embodiments, the electronic device is a mobile electronic device.

In another aspect, the present disclosure provides a method of performing a clinical assessment of Parkinson's disease on a subject, comprising: (i) receiving sensor data from one or more sensors; (ii) using one or more programmed computer processors to process the sensor data or features extracted therefrom using a trained machine-learning algorithm to generate an output indicative of the state of the neurological disease, disorder, or condition of the subject; (iii) based at least in part on the generated output, performing the clinical assessment on the subject, wherein the clinical assessment comprises a clinical examination, a clinical questionnaire, a radiological brain imaging test, or a polysomnography test.

In some embodiments, the method further comprises using a mobile electronic device to record the sensor data. In some embodiments, the electronic device is a mobile electronic device. In some embodiments, the motor function data is processed by the electronic device. In some embodiments, the motor function data is processed by a computer system separate from the electronic device. In some embodiments, the computer system is a distributed computer system in network communication with the electronic device.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the disclosure are set forth with particularity in the appended claims. A better understanding of the features and advantages of the present disclosure are obtained by reference to the following detailed description that sets forth illustrative embodiments, in which the principles of the disclosure are utilized, and the accompanying drawings (also "Figure" and "FIG." herein), of which:

FIG. 1B illustrates an example of an application GUI for a Balance Exercise task.

FIG. 1C illustrates an example of an application GUI for a Walking Exercise task.

FIGS. 1F-1G illustrate an example of an application GUI for a Reaction Time Exercise task.

FIG. 2A illustrates example sensor data obtained during the performance of a Voice Exercise task by a subject.

FIG. 2B illustrates example sensor data obtained during the performance of a Balance Exercise task by a subject.

FIG. 2C illustrates example sensor data obtained during the performance of a Walking Exercise task by a subject.

FIG. 2D illustrates example sensor data obtained during the performance of a Finger Tapping Exercise task by a subject.

FIG. 2E illustrates example sensor data obtained during the performance of a Reaction Time Exercise task by a subject.

FIG. 2F illustrates example sensor data obtained during the performance of a Rest Tremor Exercise task by a subject.

FIG. 2G illustrates example sensor data obtained during the performance of a Postural Tremor Exercise task by a subject.

Figure 3:
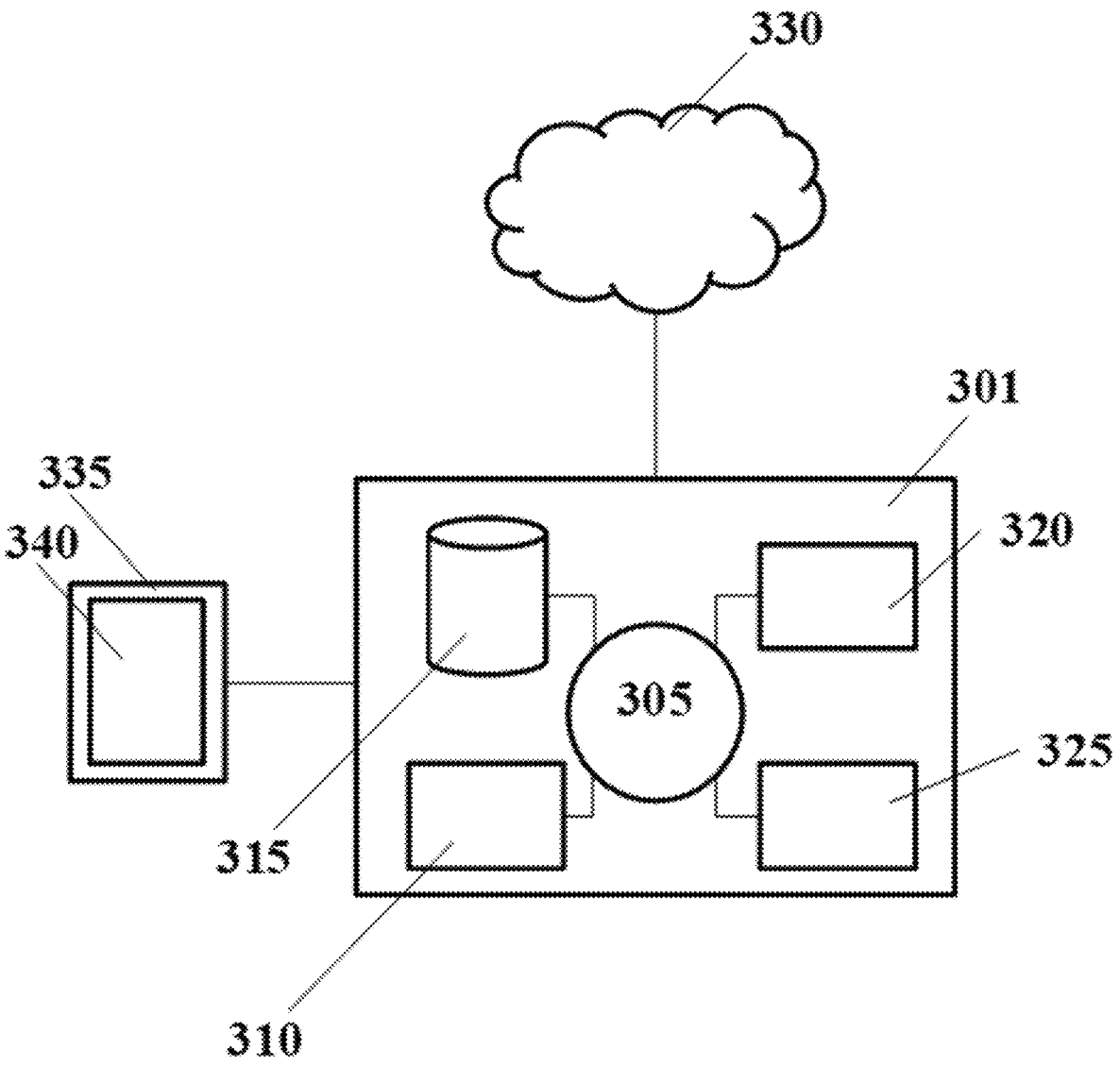

FIG. 3 shows a computer system that is programmed or otherwise configured to implement methods provided herein.

Figure 4A:
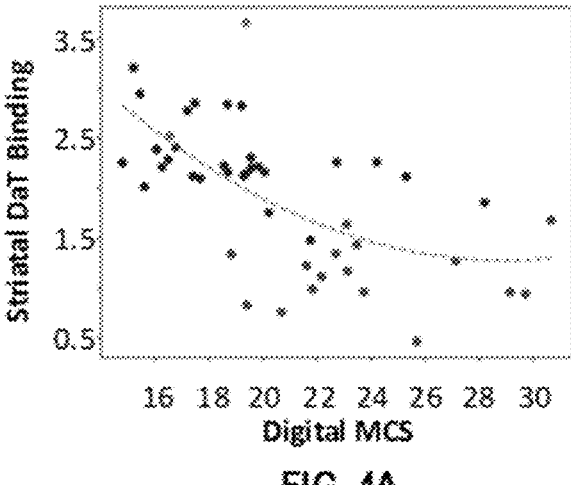

FIG. 4A illustrates a correlation between a digital motor composite score (MCS) obtained from subjects during the performance of motor tasks and a Dopamine Active Transporter tomography scan (DaTscan) binding ratio of the striatum ipsilateral to the worst motoric clinically affected side of the subjects.

Figure 4B:
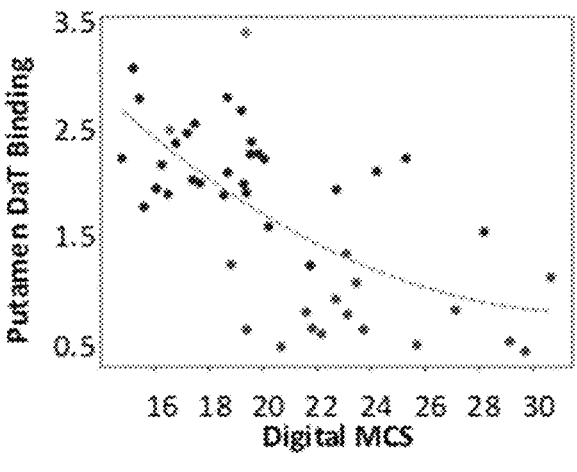

FIG. 4B illustrates a correlation between a digital MCS obtained from subjects during the performance of motor tasks and a DaTscan binding ratio of the putamen ipsilateral to the worst motoric clinically affected side of the subjects.

Figure 4C:
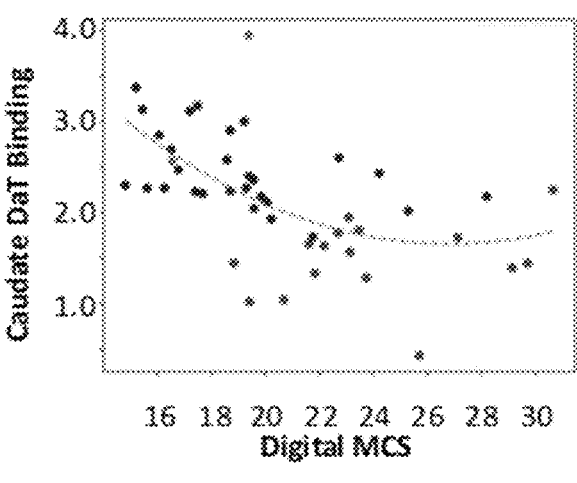

FIG. 4C illustrates a correlation between a digital MCS obtained from subjects during the performance of motor tasks and a DaTscan binding ratio of the caudate nucleus contralateral to the worst motoric clinically affected side of the subjects.

Figure 5A:
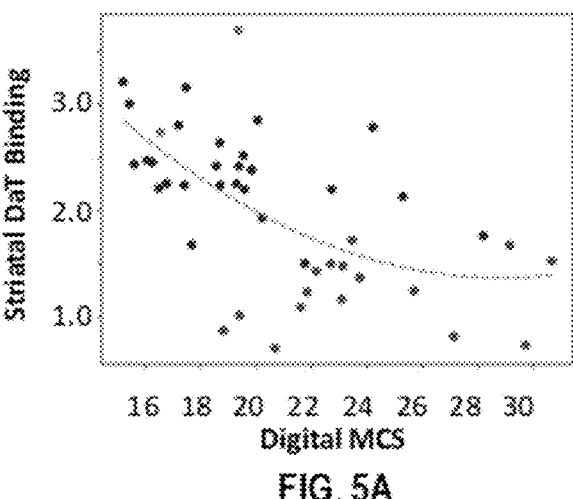

FIG. 5A illustrates a correlation between a digital MCS obtained from subjects during the performance of motor tasks and a DaTscan binding ratio of the striatum contralateral the worst motoric clinically affected side of the subjects.

Figure 5B:
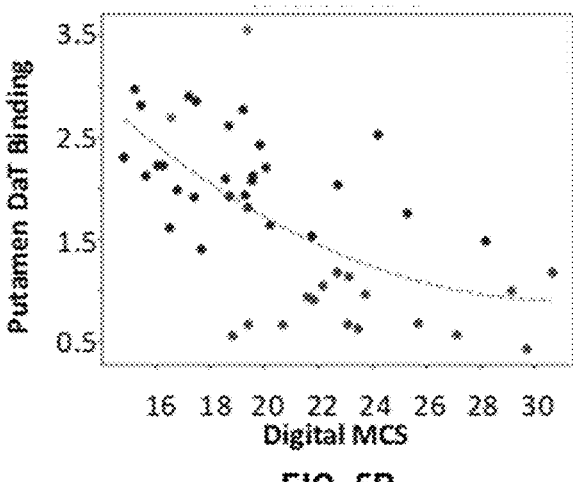

FIG. 5B illustrates a correlation between a digital MCS obtained from subjects during the performance of motor tasks and a DaTscan binding ratio of the putamen contralateral the worst motoric clinically affected side of the subjects.

Figure 5C:
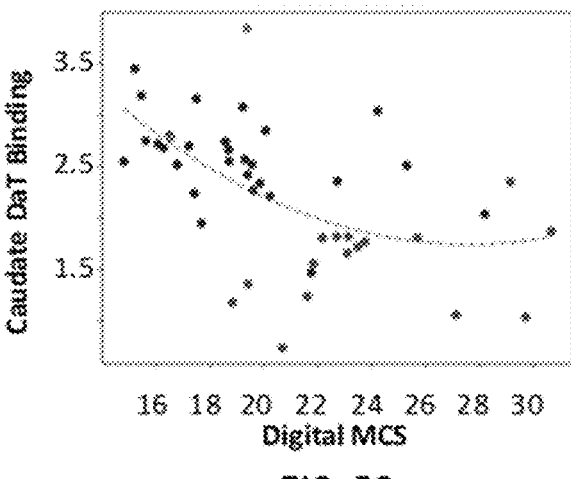

FIG. 5C illustrates a correlation between a digital MCS obtained from subjects during the performance of motor tasks and a DaTscan binding ratio of the caudate nucleus ipsilateral the worst motoric clinically affected side of the subjects.

DETAILED DESCRIPTION

While various embodiments of the invention have been shown and described herein, it is obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Various terms used throughout the present description may be read and understood as follows, unless the context indicates otherwise: "or" as used throughout is inclusive, as though written "and/or"; singular articles and pronouns as used throughout include their plural forms, and vice versa; similarly, gendered pronouns include their counterpart pronouns so that pronouns should not be understood as limiting anything described herein to use, implementation, performance, etc. by a single gender; "exemplary" should be understood as "illustrative" or "exemplifying" and not necessarily as "preferred" over other embodiments. Further definitions for terms may be set out herein; these may apply to prior and subsequent instances of those terms, as are understood from a reading of the present description. Whenever the term "at least," "greater than," or "greater than or equal to" precedes the first numerical value in a series of two or more numerical values, the term "at least," "greater than" or "greater than or equal to" applies to each of the numerical values in that series of numerical values. For example, 12,569,185 B2

11 12 greater than or equal to 1, 2, or 3 is equivalent to greater than or equal to 1, greater than or equal to 2, or greater than or equal to 3.

Whenever the term "no more than," "less than," or "less than or equal to" precedes the first numerical value in a series of two or more numerical values, the term "no more than," "less than," or "less than or equal to" applies to each of the numerical values in that series of numerical values. For example, less than or equal to 3, 2, or 1 is equivalent to less than or equal to 3, less than or equal to 2, or less than or equal to 1.

The term "subject," as used herein, generally refers to a human such as a patient. The subject may be a person (e.g., a patient) with a neurological disease, disorder, or condition, or a person that has been treated for a neurological disease, disorder, or condition, or a person that is being monitored for a neurological disease, disorder, or condition, or a person that is suspected of having the neurological disease, disorder, or condition, or a person that does not have or is not suspected of having the neurological disease, disorder, or condition. The neurological disease, disorder, or condition may be an infectious disease, an immune disorder or disease, a cancer, a genetic disease, a degenerative disease, a lifestyle disease, an injury, a rare disease, or an age related disease. The infectious disease may be caused by bacteria, viruses, fungi and/or parasites. For example, the disease or disorder may comprise Parkinson's disease (PD), atypical parkinsonism, or prodromal stage PD, parasomnia, REM Sleep Behavior Disorder (RBD), dementia (e.g., dementia with Lewy bodies), progressive supranuclear palsy, corticobasal degeneration or multiple system atrophy.

Subject or patient assessment may require collection and analysis of motor function information over a period of time that may be sufficient to detect clinically relevant signs of the patient having a state of a neurological disease, disorder, or condition. For the example, the subject or patient who has been treated for a neurological disease, disorder, or condition at a hospital or other clinical setting may need to be monitored for a change of state of the disease, disorder, or condition. For example, a subject or patient who exhibits loss of motor or cognitive function in a clinical assessment may need to be monitored for indications of Parkinson's disease (PD), atypical parkinsonism, or prodromal stage PD, parasomnia, REM Sleep Behavior Disorder (RBD), dementia (e.g., dementia with Lewy bodies), progressive supranuclear palsy, corticobasal degeneration or multiple system atrophy. Subject or patient assessment may include the performance of a clinical assessment on the patient, for example, a radiological brain imaging test or a polysomnography (PSG) test. Subject or patient assessment may detect biological indicators of a neurological disease, disorder, or condition, for example, the loss of dopamine neurons or a change in function of the dopamine system in PD. Such subject or patient assessment may be performed in a hospital or other clinical setting using specialized equipment such the rotating X-ray tubes of tomographic scans, magnetic resonance or electrodes of a polysomnography study. However, subject or patient assessment outside of a clinical setting (e.g., a hospital) may pose challenges for non-invasive collection of motor function information and accurate assessment of the state of a neurological disease, disorder, or condition.

Recognized herein is the need for systems and methods for subject or patient assessment by the collection of motor function information. Such analysis of motor function information of a subject may be performed by a mobile electronic device (e.g., at the subject's home, instead of a clinical setting such as a hospital) over a period of time to generate an output indicative of the state of a neurological disease, disorder, or condition.

The present disclosure provides systems and methods that may advantageously collect and analyze motor function information from a subject over a period of time to accurately and non-invasively generate an output indicative of the state of a neurological disease, disorder, or condition. Such systems and methods may allow subjects or patients with elevated risk of a neurological disease, disorder, or condition to be accurately monitored for recurrence outside of a clinical setting, thereby improving the accuracy of detection of the state of a neurological disease, disorder, or condition; reducing clinical health care costs; and improving quality of life. For example, such systems and methods may produce accurate detections or predictions of likelihood of a disease, disorder, or condition that are clinically actionable by physicians (or other health care workers) toward deciding whether to enroll a patient into a clinical trial. As another example, such systems and methods may enable in-home patient assessment, thereby increasing patients' quality of life compared to making frequent visits to clinical care sites.

The collected and transmitted motor function information may be aggregated, for example, by batching and uploading to a computer server (e.g., a secure cloud database), where artificially intelligent algorithms may analyze the data in a continuous or real-time manner. If an adverse health condition (e.g., deterioration of the patient's state, occurrence or recurrence of a disease, disorder, or condition) is detected or predicted, the computer server may send a notification to a health care provider (e.g., a general practitioner and/or treating physician). The health care provider may subsequently perform follow-up care, such as contacting the subject or patient and requesting that the subject or patient return to the hospital for further treatment or clinical inspection (e.g., monitoring, diagnosis, or prognosis). Alternatively, or in combination, the health care provider may prescribe a treatment or a clinical procedure to be administered to the subject or patient based on the notification.

Assessment System Overview

An assessment system may be used to collect and analyze motor function information from a subject over a period of time to perform a clinical assessment of a subject suspected of having or having a disease, disorder, or condition (e.g., a neurological disorder such as Parkinson's disease). The assessment system may comprise a mobile electronic device. The assessment system may be used in a hospital or other clinical setting or in a home setting of the subject.

The assessment system may comprise a mobile electronic device (e.g., a smartphone or a tablet computer), a mobile phone application, a database, and an artificial intelligence-based analytics engine to perform a clinical assessment of a subject (e.g., a subject suspected of having a neurological disorder) by detecting or predicting an adverse health condition (e.g., deterioration of the subject's state, occurrence or recurrence of a neurological disease or disorder, or condition) in the subject.

The mobile electronic device (e.g., a smartphone or a tablet computer) may be configured to measure, collect, and/or record sensor data, such as data obtained during the performance of a motor task by the subject (e.g., a task measuring vocalization, balance, gait, tapping, reaction time, resting tremor, or postural tremor, FIG. 1A-1I). Examples of sensor data may include data collected by an accelerometer, a touch screen sensor, a video sensor, or an audio sensor (FIG. 2A-2G). The data may be measured, collected, and/or recorded in real-time by the mobile electronic device. The device may be used to assess a subject (e.g., patient) over a period of time based on the acquired sensor data, for example, by detecting or predicting an adverse health condition (e.g., deterioration of the patient's state, occurrence or recurrence of a disease, disorder, or condition) in the subject over the period of time.

The mobile electronic device (e.g., a smartphone or a tablet computer) may comprise sensors configured to measure, collect, and/or record sensor data. The sensors may comprise an accelerometer, e.g., a triaxial accelerometer. The sensors may comprise a touch screen sensor, e.g., a resistive touch sensor, capacitive touch sensor, or a surface acoustic wave sensor. The sensors may comprise a video sensor, e.g., a camera. The sensors may comprise an audio sensor, e.g., a microphone. The sensors may comprise a gyroscope sensory, e.g., an angular velocity sensor. Sensor data measured, collected, and/or recorded by a sensor may comprise inertial measurement units (e.g., sensor data collected by an accelerometer), coordinates of an electronic display (e.g., data collected by a touch screen sensor), video recordings (e.g., data collected by a video sensor), audio recordings (e.g., data collected by an audio sensor), and event times.

The mobile application may be configured to allow a user to pair with, control, and view data from the mobile electronic device. The mobile application may comprise a graphical user interface (GUI) to allow the user to view trends, statistics, and/or notifications generated based on their measured, collected, or recorded sensor data (e.g., currently measured data, previously collected or recorded data, or a combination thereof). For example, the GUI may allow the user to view historical or average trends of a set of sensor data over a period of time (e.g., on an hourly basis, on a daily basis, on a weekly basis, on a monthly basis or on an annual basis). The GUI may provide instruction to the subject on the method of performance of motor tasks (e.g., a task measuring vocalization, balance, gait, tapping, reaction time, resting tremor, or postural tremor, FIGS. 1A-1I), and the mobile electronic device may measure, collect, and/or record sensor data during the performance of the motor tasks (FIGS. 2A-2G). The mobile application may further communicate with a web-based software application, which may be configured to store and analyze the recorded sensor data. For example, the recorded sensor data may be stored in a database (e.g., a computer server or on a cloud network) for real-time or future processing and analysis.

The mobile application may be further configured acquire, record, receive, or process patient reported data. For example, the mobile application device may process patient reported outcome measure (PROM) data. The PROM data may comprise quality of life, pain, or fatigue information reported by the patient. The mobile application may be configured to record, receive, or process data from a behavioral test of cognitive function. The behavioral test of cognitive function may be a Montreal Cognitive Assessment (MoCA) or equivalent or a digital test of processing speed, working memory, or executive function. The PROM data or the data from the behavioral test of cognitive function may be provided to the mobile application by the patient or by a health care provider.

Health care providers, such as physicians and treating teams of a patient (e.g., the subject) may have access to patient notifications, data (e.g., sensor data), and/or predictions or assessments generated from such data. Such access may be provided by a web-based dashboard (e.g., a GUI). The web-based dashboard may be configured to display, for example, patient metrics, recent notifications, and/or prediction of health outcomes (e.g., rate or likelihood of deterioration and/or a neurological condition, e.g., Parkinson's disease). Using the web-based dashboard, health care providers may determine clinical decisions or outcomes based at least in part on such displayed notifications, data, and/or predictions or assessments generated from such data.

For example, a physician may instruct the subject or patient to undergo one or more clinical tests at the hospital or other clinical site, based at least in part on patient metrics or on notifications detecting or predicting an adverse health condition (e.g., deterioration of the patient's state, occurrence or recurrence of a neurological disease, disorder, or condition) in the subject over a period of time. The assessment system may generate and transmit such notifications to health care providers when a certain predetermined criterion is met (e.g., a minimum threshold for a likelihood of deterioration of the subject's state, occurrence of a disease, disorder, or condition).

Such a minimum threshold may be, for example, at least about a 5% likelihood, at least about a 10% likelihood, at least about a 20% likelihood, at least about a 25% likelihood, at least about a 30% likelihood, at least about a 35% likelihood, at least about a 40% likelihood, at least about a 45% likelihood, at least about a 50% likelihood, at least about a 55% likelihood, at least about a 60% likelihood, at least about a 65% likelihood, at least about a 70% likelihood, at least about a 75% likelihood, at least about an 80% likelihood, at least about a 85% likelihood, at least about a 90% likelihood, at least about a 95% likelihood, at least about a 96% likelihood, at least about a 97% likelihood, at least about a 98% likelihood, or at least about a 99% likelihood.

As another example, a physician may prescribe a therapeutically effective dose of a treatment (e.g., drug), a clinical procedure, or further clinical assessment to be administered to the subject or patient based at least in part on patient metrics or on notifications detecting or predicting an adverse health condition (e.g., Parkinson's disease, deterioration of the patient's state, occurrence or recurrence of a neurological disease, disorder, or condition) in the subject over a period of time.

For example, based at least in part on an output generated by the assessment system, the physician may prescribe a radiological brain imaging test (e.g., a Dopamine Active Transporter tomography scan, DaTscan), a polysomnography (PSG) test, a Movement Disorder Society-Unified Parkinson's Disease Rating Scale (MDS-UPDRS) examination, a Montreal Cognitive Assessment (MoCA) or equivalent, a Purdue Pegboard Test, or a Timed Up and Go Test, or medication. Such a prescription of a therapeutically effective dose of a treatment (e.g., drug), a clinical procedure, or further clinical assessment may be determined without requiring an in-person clinical appointment with the prescribing physician.

The physician may prescribe a radiological imaging test (e.g., to detect loss of dopaminergic neurons), such as a tomography scan (e.g., a Dopamine Active Transporter ioflupane ($^{123}$I) single photon emission tomography scan) or a physiological test (e.g., to detect and characterize indications of onset of a neurological disorder), such as a polysomnography (PSG) test (e.g., a PSG comprising a sleep study). Radiological brain imaging tests may measure, determine, or visualize dopamine neuron loss or the dopamine system in a brain area (e.g., the striatum, the putamen, or the caudate nucleus). PSG tests may be prescribed to detect and diagnose a prodromal stage of Parkinson's disease or a parasomnia (e.g., REM Sleep Behavior Disorder, RBD).

Behavioral tests such as the MDS-UPDRS-III motor examination, the Purdue Pegboard Test, or the Timed Up and Go Test may be prescribed to quantify a severity of degradation of motor function. MoCA may be prescribed to quantify a severity of cognitive decline. An output generated by the assessment system may correlate with a result of a clinical assessment. For example, the generated output may correlate with measures of dopamine neuron loss, e.g., DaTscan tracer uptake or with a DaTscan striatal binding ration.

The assessment system may comprise a mobile electronic device, a mobile device application, and a web database. The system may comprise a sensor device, a mobile interface (e.g., graphical user interface, or GUI) of the mobile device application (e.g., to enable a user to control collection, measurement, recording, storage, and/or analysis of sensor data to generate an output indicative of the state of a neurological disease, disorder, or condition), and computer hardware and/or software for storage and/or analytics of the collected sensor data (e.g., motor function information).

The mobile device application of the assessment system may utilize or access external capabilities of artificial intelligence techniques to develop signatures for patient deterioration and disease states. The web-based software may further use these signatures to accurately predict a future onset of a deterioration (e.g., weeks, months, or years earlier than with traditional clinical care). Using such a predictive capability, health care providers (e.g., physicians) may be able to make informed, accurate risk-based assessments, diagnoses, and/or categorizations.

The mobile device application may analyze acquired sensor data from a subject (patient) to generate a likelihood or predicted risk of the subject having a pre-determined outcome of a clinical assessment (e.g., dopamine neuron loss as measure by a DaTscan, deterioration of motor function, or occurrence or recurrence of a neurological disease or disorder, or condition). For example, the mobile device application may apply a trained (e.g., prediction) algorithm to the acquired sensor data to generate the likelihood or predicted risk of the subject having an outcome of a clinical assessment (e.g., dopamine neuron loss as measure by a DaTscan, deterioration of motor function, or occurrence or recurrence of a neurological disease or disorder, or condition). The trained algorithm may comprise an artificial intelligence based algorithm, such as a machine learning based algorithm, configured to process the acquired sensor data to generate an output indicative of the state of a neurological disease, disorder, or condition. The machine learning algorithm may be trained using clinical datasets from one or more cohorts of patients, e.g., using clinical data of the patients (e.g., motor function data) as inputs and known clinical health outcomes (e.g., state of a neurological disease, disorder, or condition) of the patients as outputs to the machine learning algorithm. In some embodiments, in addition to sensor data, the mobile device application may acquire PROM data or data from a behavioral test of cognitive function to generate a likelihood or predicted risk of a subject having a pre-determined outcome of a clinical assessment.

Machine Learning Algorithms

The machine learning algorithm may comprise one or more machine learning algorithms. Examples of machine learning algorithms may include a support vector machine (SVM), a naïve Bayes classification, a random forest, a neural network (such as a deep neural network (DNN), a recurrent neural network (RNN), a deep RNN, a long short-term memory (LSTM) recurrent neural network (RNN), or a gated recurrent unit (GRU) recurrent neural network (RNN)), deep learning, or other supervised learning algorithm or unsupervised learning algorithm for classification and regression. The machine learning algorithm may be trained using one or more training datasets corresponding to subject or patient data.

Training datasets may be generated from, for example, one or more cohorts of subjects or patients having common clinical characteristics (features) and clinical outcomes (labels). Training datasets may comprise a set of features and labels corresponding to the features. Features may correspond to algorithm inputs comprising patient demographic information derived from electronic medical records (EMR) and medical observations. Features may comprise clinical characteristics such as, for example, certain ranges or categories of motor function measurements, such as measurements of vocalization, balance, gait, tapping, reaction time, resting tremor, or postural tremor (FIG. 2A-2G). Features may comprise subject information such as subject age, sex, ethnicity, subject medical history, disease durations, genetic profile, other medical conditions, current or past medications, and time since the last observation. For example, a set of features collected from a given subject at a given time point may collectively serve as a motor function score, which may be indicative of a health state or status of the patient at the given time point.

For example, ranges of motor function measurements may be expressed as a plurality of disjoint continuous ranges of continuous measurement values, and categories of motor function measurements may be expressed as a plurality of disjoint sets of measurement values (e.g., {"high", "low"}, {"high", "normal"}, {"low", "normal"}, {"high", "borderline high", "normal", "low"}, etc.). Clinical characteristics may also include clinical labels indicating the patient's health history, such as a diagnosis of a disease or disorder, a previous administration of a clinical treatment (e.g., a drug, a surgical treatment, a physical therapy, etc.), behavioral factors, or other health status.

Labels may comprise clinical outcomes or the associated likelihood or probability of clinical outcomes, from either one or multiple sources, such as, for example, a presence, absence, diagnosis, severity, or prognosis of an adverse health condition (e.g., deterioration of the patient's state, occurrence or recurrence of a neurological disease, disorder, or condition) in the patient. Clinical outcomes may include a temporal characteristic associated with the presence, absence, diagnosis, severity, state, or prognosis of the neurological disease, disorder, or condition in the patient. For example, temporal characteristics may be indicative of the patient having had an onset of the neurological disease, disorder, or condition (e.g., Parkinson's disease) within a certain period of time after a previous clinical outcome (e.g., undergoing clinical tests, such as a radiological scan or a polysomnography test.). Such a period of time may be, for example, about 4 weeks, about 1 month, about 2 months, about 3 months, about 4 months, about 6 months, about 8 months, about 10 months, about 1 year, about 2 years, about 3 years, about 4 years, about 5 years, about 6 years, about 7 years, about 8 years, about 9 years, about 10 years, about 12 years, about 15 years, about 17 years, about 20 years, or more than about 20 years.

Input features may be structured by aggregating the data into bins or alternatively using a one-hot encoding with the time since the last observation included. Inputs may also include feature values or vectors derived from the previously mentioned inputs, such as cross-correlations calculated between separate sensor measurements over a fixed period of time, and the discrete derivative or the finite difference between successive measurements. Such a period of time may be, for example, about 1 hour, about 2 hours, about 3 hours, about 4 hours, about 6 hours, about 8 hours, about 10 hours, about 12 hours, about 14 hours, about 16 hours, about 18 hours, about 20 hours, about 22 hours, about 24 hours, about 2 days, about 3 days, about 4 days, about 5 days, about 6 days, about 7 days, about 10 days, about 2 weeks, about 3 weeks, about 4 weeks, about 1 month, about 2 months, about 3 months, about 4 months, about 6 months, about 8 months, about 10 months, about 1 year, or more than about 1 year.

Training records may be constructed from sequences of observations. Such sequences may comprise a fixed length for ease of data processing. For example, sequences may be zero-padded or selected as independent subsets of a single patient's records.

The machine learning algorithm may process the input features (e.g., input features comprising sensor data) to generate an output value indicative of the state of a neurological disease, disorder, or condition. The machine learning algorithm may process the input features to generate outputs comprising one or more classifications, one or more predictions, or a combination thereof. For example, such classifications or predictions may include a binary classification of a disease or a non-disease state, a classification between a group of categorical labels (e.g., 'no Parkinson's disease', 'Parkinson's disease apparent', and 'Parkinson's disease likely'), a predicted risk or likelihood (e.g., relative likelihood or probability) of developing or having a particular disease or disorder (e.g., Parkinson's disease) or a pre-determined outcome of a clinical assessment (e.g., loss of dopamine neurons), a generated output indicative of a state of a neurological condition (e.g., a level of dopaminergic neuron loss) or indicative of a phase of a neurological condition (e.g., prodromal Parkinson's disease), a prediction of the time at which the patient is expected to have developed the disease or disorder, and a confidence interval for any numeric predictions. Further, the generated output may comprise an indication of whether a subject is likely to benefit from enrollment into a clinical trial. The generated output may provide sufficient evidence to detect the neurological disease, disorder, or condition. Various machine learning techniques may be cascaded such that the output of a machine learning technique may also be used as input features to subsequent layers or subsections of the machine learning algorithm.

Input features processed by the machine learning algorithm may comprise salient features (e.g., the most salient features of the sensor data). The generated output may comprise a set of the salient features. The generated output may comprise less than about 200 salient features, less than about 150 salient features, less than about 125 salient features, less than about 100 salient features, less than about 90 salient features, less than about 80 salient features, less than about 75 salient features, less than about 70 salient features, less than about 65 salient features, less than about 60 salient features, less than about 55 salient features, less than about 50 salient features, less than about 45 salient features, less than about 40 salient features, less than about 35 salient features, less than about 30 salient features, less than about 25 salient features, less than about 20 salient features, or less than about 10 salient features.

In order to train the machine learning model (e.g., by determining weights and correlations of the model) to generate classifications or predictions, the model can be trained using datasets. Such datasets may be sufficiently large to generate statistically significant classifications or predictions. Datasets may comprise measurements generated by clinical assessments of motor function loss, for example: (a) the composite clinical motor score (CMS), calculated by combining components of (1) the Movement Disorders Society-Unified Parkinson's Disease Rating Scale (MDS-UPDRS) II and/or III motor examination score; (2) the Purdue Pegboard Test, (3) the Timed Up and Go Test; (b) measurements from the MDS-UPDRS, the Purdue Pegboard Test, or the Timed Up and Go Test alone or in combination; (c) combined sub-score measurements from the MDS-UP-DRS, the Purdue Pegboard Test, or the Timed Up and Go Test; or (d) other clinically validated measures alone or in combination and motor function measurements collected using mobile electronic devices of the present disclosure.

In some cases, datasets are annotated or labeled. For example, to identify and label the onset of REM Sleep Behavior Disorder (RBD) in training records from polysom-nography tests.

Datasets may be split into subsets (e.g., discrete or over-lapping), such as a training dataset, a development dataset, and a test dataset. For example, a dataset may be split into a training dataset comprising 80% of the dataset, a devel-opment dataset comprising 10% of the dataset, and a test dataset comprising 10% of the dataset. The training dataset may comprise about 10%, about 20%, about 30%, about 40%, about 50%, about 60%, about 70%, about 80%, or about 90% of the dataset. The development dataset may comprise about 10%, about 20%, about 30%, about 40%, about 50%, about 60%, about 70%, about 80%, or about 90% of the dataset. The test dataset may comprise about 10%, about 20%, about 30%, about 40%, about 50%, about 60%, about 70%, about 80%, or about 90% of the dataset. Training sets (e.g., training datasets) may be selected by random sampling of a set of data corresponding to one or more patient cohorts to ensure independence of sampling. Alternatively, training sets (e.g., training datasets) may be selected by proportionate sampling of a set of data corre-sponding to one or more patient cohorts to ensure indepen-dence of sampling. Cross-validation schemes may be used, for example, leave-one-subject-out (LOSO).

To improve the accuracy of model predictions and reduce overfitting of the model, the datasets may be augmented to increase the number of samples within the training set. For example, data augmentation may comprise rearranging the order of observations in a training record. To accommodate datasets having missing observations, methods to impute missing data may be used, such as forward-filling, back-filling, linear interpolation, and multi-task Gaussian pro-cesses. Datasets may be filtered to remove confounding factors. To accommodate data imbalance, different sampling techniques may be employed.

The machine learning algorithm may comprise one or more neural networks, such as a deep neural network (DNN), a recurrent neural network (RNN), or a deep RNN. The recurrent neural network may comprise units which can be long short-term memory (LSTM) units or gated recurrent units (GRU). For example, as shown in FIG. 9, the machine learning algorithm may comprise an algorithm architecture comprising a long short-term memory (LSTM) recurrent neural network (RNN), with a set of input features such as motor function observations, patient medical history, and patient demographics. Neural network techniques, such as dropout or regularization, may be used during training the machine learning algorithm to prevent overfitting. To accommodate data imbalance, observations may be weighted during the training process.

When the machine learning algorithm generates an output indicative of the state of a neurological disease, disorder, or condition, a notification or alert may be generated and transmitted to a health care provider, such as a physician, nurse, or other member of the patient's treating team within a hospital. Notifications may be transmitted via an automated phone call, a short message service (SMS) or multimedia message service (MMS) message, an e-mail, or a notification within a dashboard. The notification may comprise output information such as a prediction of a disease, disorder, or condition, a likelihood of the predicted disease, disorder, or condition, a time until an expected onset of the disease, disorder, or condition, a confidence interval of the likelihood or time, a recommended course of treatment for the disease, disorder, or condition, or a recommended clinical test to further assess the subject (e.g., at DaTscan or a polysomnography test). The LSTM recurrent neural network may comprise a plurality of sub-networks, each of which is configured to generate a classification or prediction of a different type of output information (e.g., a Parkinson's/non-Parkinson's disease classification and a severity of motor function loss).

To validate the performance of the machine learning algorithm model, different performance metrics may be generated. For example, an area under the receiver-operating curve (AUROC) may be used to determine the diagnostic capability of the machine learning algorithm. For example, the machine learning algorithm may use classification thresholds which are adjustable, such that specificity and sensitivity are tunable, and the receiver-operating curve (ROC) can be used to identify the different operating points corresponding to different values of specificity and sensitivity. The validation scheme may incorporate asymmetric costs of a false positive and a false negative.

In some cases, such as when datasets are not sufficiently large, cross-validation may be performed to assess the robustness of a machine learning algorithm model across different training and testing datasets.

In some cases, while a machine learning algorithm model may be trained using a dataset of records which are a subset of a single subject's observations, the performance of the algorithm model's discrimination ability (e.g., as assessed using an AUROC) is calculated using the entire record for a patient. To calculate performance metrics such as sensitivity, specificity, accuracy, positive predictive value (PPV), negative predictive value (NPV), AUPRC, AUROC, or similar, the following definitions may be used. A "false positive" may refer to an outcome in which if a notification or alert has been incorrectly or prematurely activated (e.g., before the actual onset of, or without any onset of, a disease state or condition such as Parkinson's disease) fires too early. A "true positive" may refer to an outcome in which a notification or alert has been activated at the correct time (within a predetermined buffer or tolerance), and the patient's record indicates the disease or condition (e.g., Parkinson's disease). A "false negative" may refer to an outcome in which no notification or alert has been activated, but the patient's record indicates the disease or condition (e.g., Parkinson's disease). A "true negative" may refer to an outcome in which no notification or alert has been activated, and the patient's record does not indicate the disease or condition (e.g., Parkinson's disease).

The machine learning algorithm may be trained until certain predetermined conditions for accuracy or performance are satisfied, such as having minimum desired values corresponding to clinical assessment or diagnostic accuracy measures (e.g., dopamine neuron loss measured by a DaTscan). For example, the diagnostic accuracy measure may correspond to prediction of a likelihood of occurrence of an adverse health condition such as deterioration or a disease or disorder (e.g., a state of a neurological disease, disorder, or condition) in the subject. As another example, the clinical assessment or diagnostic accuracy measure may correspond to prediction of a likelihood of deterioration or recurrence of an adverse health condition such as a disease or disorder for which the subject has previously been treated. For example, a clinical assessment or diagnostic accuracy measure may correspond to prediction of likelihood of deterioration of motor function in a subject who has previously been treated for prodromal phase Parkinson's disease. Examples of diagnostic accuracy measures may include sensitivity, specificity, positive predictive value (PPV), negative predictive value (NPV), accuracy, area under the precision-recall curve (AUPRC), and area under the curve (AUC) of a Receiver Operating Characteristic (ROC) curve (AUROC) corresponding to the diagnostic accuracy of detecting or predicting an adverse health condition. For probabilistic predictions, where the focus is likelihood or probability of an event of occurrence, Brier score and calibration curves may be used for validation.

For example, such a predetermined condition may be that the sensitivity of predicting a state of a neurological disease, disorder, or condition (e.g., onset of Parkinson's disease) comprises a value of, for example, at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99%.

As another example, such a predetermined condition may be that the specificity of predicting a state of a neurological disease, disorder, or condition (e.g., onset of Parkinson's disease) comprises a value of, for example, at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99%.

As another example, such a predetermined condition may be that the positive predictive value (PPV) of predicting a state of a neurological disease, disorder, or condition (e.g., onset of Parkinson's disease) comprises a value of, for example, at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99%.

As another example, such a predetermined condition may be that the negative predictive value (NPV) of predicting a state of a neurological disease, disorder, or condition (e.g., onset of Parkinson's disease) comprises a value of, for example, at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99%.

As another example, such a predetermined condition may be that the area under the curve (AUC) of a Receiver Operating Characteristic (ROC) curve (AUROC) of predicting a state of a neurological disease, disorder, or condition (e.g., onset of Parkinson's disease) comprises a value of at least about 0.50, at least about 0.55, at least about 0.60, at least about 0.65, at least about 0.70, at least about 0.75, at least about 0.80, at least about 0.85, at least about 0.90, at least about 0.95, at least about 0.96, at least about 0.97, at least about 0.98, or at least about 0.99.

As another example, such a predetermined condition may be that the area under the precision-recall curve (AUPRC) of predicting a state of a neurological disease, disorder, or condition (e.g., onset of Parkinson's disease) comprises a value of at least about 0.10, at least about 0.15, at least about 0.20, at least about 0.25, at least about 0.30, at least about 0.35, at least about 0.40, at least about 0.45, at least about 0.50, at least about 0.55, at least about 0.60, at least about 0.65, at least about 0.70, at least about 0.75, at least about 0.80, at least about 0.85, at least about 0.90, at least about 0.95, at least about 0.96, at least about 0.97, at least about 0.98, or at least about 0.99.

In some embodiments, the trained algorithm may be trained or configured to predict a state of a neurological disease, disorder, or condition (e.g., onset of Parkinson's disease) with a sensitivity of at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99%.

In some embodiments, the trained algorithm may be trained or configured to predict a state of a neurological disease, disorder, or condition (e.g., onset of Parkinson's disease) with a specificity of at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99%.

In some embodiments, the trained algorithm may be trained or configured to predict a state of a neurological disease, disorder, or condition (e.g., onset of Parkinson's disease) with a positive predictive value (PPV) of at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99%.

In some embodiments, the trained algorithm may be trained or configured to predict a state of a neurological disease, disorder, or condition (e.g., onset of Parkinson's disease) with a negative predictive value (NPV) of at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99%.

In some embodiments, the trained algorithm may be trained or configured to predict a state of a neurological disease, disorder, or condition (e.g., onset of Parkinson's disease) with an area under the curve (AUC) of a Receiver Operating Characteristic (ROC) curve (AUROC) of at least about 0.50, at least about 0.55, at least about 0.60, at least about 0.65, at least about 0.70, at least about 0.75, at least about 0.80, at least about 0.85, at least about 0.90, at least about 0.95, at least about 0.96, at least about 0.97, at least about 0.98, or at least about 0.99.

In some embodiments, the trained algorithm may be trained or configured to predict a state of a neurological disease, disorder, or condition (e.g., onset of Parkinson's disease) with an area under the precision-recall curve (AU-PRC) of at least about 0.10, at least about 0.15, at least about 0.20, at least about 0.25, at least about 0.30, at least about 0.35, at least about 0.40, at least about 0.45, at least about 0.50, at least about 0.55, at least about 0.60, at least about 0.65, at least about 0.70, at least about 0.75, at least about 0.80, at least about 0.85, at least about 0.90, at least about 0.95, at least about 0.96, at least about 0.97, at least about 0.98, or at least about 0.99.

In some embodiments, the trained algorithm may be trained or configured to predict a state of a neurological disease, disorder, or condition (e.g., onset of Parkinson's disease) over a period of time before the actual occurrence or recurrence of the adverse health condition (e.g., a period of time including a window beginning about 4 weeks, about 1 month, about 2 months, about 3 months, about 4 months, about 6 months, about 8 months, about 10 months, about 1 year, about 2 years, about 3 years, about 4 years, about 5 years, about 6 years, about 7 years, about 8 years, about 9 years, about 10 years, about 12 years, about 15 years, about 17 years, about 20 years, or more than about 20 years prior to the onset of the health condition, and ending at the onset of the health condition).

A generated output of the machine learning algorithm may comprise an estimated motor composite score. The generated output (e.g., an output comprising an MCS) may estimate an outcome of a clinical assessment of a neurological disease, disorder, or condition. For example, the generated output comprising an MCS may estimate a composite motor score (CMS), wherein the CMS comprises an MDS-UPDRS examination score, a Purdue Pegboard Test score, a Timed Up and Go Test score, or any combination of sub-scores from these test scores or equivalent tests. For example, the generated output comprising an MCS may estimate a composite motor score (CMS) with a mean error of less than about 25 points, less than about 20 points, less than about 15 points, less than about 12 points, less than about 10 points, less than about 9 points, less than about 8 points, less than about 7 points, less than about 6 points, less than about 5 points, less than about 4 points, less than about 3 points, less than about 2 points, or less than about 1 point.

A generated output of the machine learning algorithm may correlate with an outcome of a clinical assessment of a clinical assessment of a neurological disease, disorder, or condition. The generated output may have a non-linear correlation with an outcome of a clinical assessment of a clinical assessment of a neurological disease, disorder, or condition. The generated output may have a negative correlation with an outcome of a clinical assessment of a clinical assessment of a neurological disease, disorder, or condition. The generated output may have a correlation coefficient of less than about 0, less than about negative 0.1, less than about negative 0.2, less than about negative 0.3, less than about negative 0.4, less than about negative 0.5, less than about negative 0.6, less than about negative 0.7, less than about negative 0.8, or less than about negative 0.9 with an outcome of a clinical assessment of a neurological disease, disorder, or condition. The generated output may have a correlation coefficient of greater than about 0, greater than about 0.1, greater than about 0.2, greater than about 0.3, greater than about 0.4, greater than about 0.5, greater than about 0.6, greater than about 0.7, greater than about 0.8, or greater than about 0.9 with an outcome of a clinical assessment of a neurological disease, disorder, or condition.

Systems and methods provided herein may perform predictive analytics using artificial intelligence based approaches, by collecting and analyzing sensor data (e.g., measurements of motor function) to yield output data (e.g., trends and insights into motor function measurements, and indications of a state of a neurological disease, disorder, or condition). Indications of the state of a neurological disease, disorder, or condition may comprise, for example, a likelihood of the assessed subject having a neurological disease or disorder (e.g., Parkinson's disease).

Computer Systems

The present disclosure provides computer systems that are programmed to implement methods of the disclosure. FIG. 3 shows a computer system 301 that is programmed or otherwise configured to implement methods provided herein.

The computer system 301 can regulate various aspects of the present disclosure, such as, for example, acquiring sensor data comprising data obtained during the performance of a motor task by a subject over a period of time, storing the acquired sensor data in a database, receiving sensor data from one or more sensors (e.g., an accelerometer sensor) through a wireless transceiver, and processing sensor data using a trained algorithm to generate an output indicative of the state of a health condition (e.g., a neurological disease, disorder, or condition). The computer system 301 can be an electronic device of a user or a computer system that is remotely located with respect to the electronic device. The electronic device can be a mobile electronic device.

The computer system 301 includes a central processing unit (CPU, also "processor" and "computer processor" herein) 305, which can be a single core or multi core processor, or a plurality of processors for parallel processing. The computer system 301 also includes memory or memory location 310 (e.g., random-access memory, read-only memory, flash memory), electronic storage unit 315 (e.g., hard disk), communication interface 320 (e.g., network adapter) for communicating with one or more other systems, and peripheral devices 325, such as cache, other memory, data storage and/or electronic display adapters. The memory 310, storage unit 315, interface 320 and peripheral devices 325 are in communication with the CPU 305 through a communication bus (solid lines), such as a motherboard. The storage unit 315 can be a data storage unit (or data repository) for storing data. The computer system 301 can be operatively coupled to a computer network ("network") 330 with the aid of the communication interface 320. The network 330 can be the Internet, an internet and/or extranet, or an intranet and/or extranet that is in communication with the Internet.

The network 330 in some cases is a telecommunication and/or data network. The network 330 can include one or more computer servers, which can enable distributed computing, such as cloud computing. For example, one or more computer servers may enable cloud computing over the network 330 ("the cloud") to perform various aspects of analysis, calculation, and generation of the present disclosure, such as, for example, acquiring sensor data comprising data obtained during the performance of a motor task by a subject over a period of time, storing the acquired sensor data in a database, receiving sensor data from one or more sensors (e.g., an accelerometer sensor) through a wireless transceiver, and processing sensor data using a trained algorithm to generate an output indicative of the state of a health condition (e.g., a neurological disease, disorder, or condition). Such cloud computing may be provided by cloud computing platforms such as, for example, Amazon Web Services (AWS), Microsoft Azure, Google Cloud Platform, and IBM cloud. The network 330, in some cases with the aid of the computer system 301, can implement a peer-to-peer network, which may enable devices coupled to the computer system 301 to behave as a client or a server.

The CPU 305 can execute a sequence of machine-readable instructions, which can be embodied in a program or software. The instructions may be stored in a memory location, such as the memory 310. The instructions can be directed to the CPU 305, which can subsequently program or otherwise configure the CPU 305 to implement methods of the present disclosure. Examples of operations performed by the CPU 305 can include fetch, decode, execute, and writeback.

The CPU 305 can be part of a circuit, such as an integrated circuit. One or more other components of the system 301 can be included in the circuit. In some cases, the circuit is an application specific integrated circuit (ASIC).

The storage unit 315 can store files, such as drivers, libraries and saved programs. The storage unit 315 can store user data, e.g., user preferences and user programs. The computer system 301 in some cases can include one or more additional data storage units that are external to the computer system 301, such as located on a remote server that is in communication with the computer system 301 through an intranet or the Internet.

The computer system 301 can communicate with one or more remote computer systems through the network 330. For instance, the computer system 301 can communicate with a remote computer system of a user. Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), personal digital assistants, or personal fitness trackers (e.g., Apple® Watch, FitBit® Watch). The user can access the computer system 301 via the network 330.

Methods as described herein can be implemented by way of machine (e.g., computer processor) executable code stored on an electronic storage location of the computer system 301, such as, for example, on the memory 310 or electronic storage unit 315. The machine executable or machine readable code can be provided in the form of software. During use, the code can be executed by the processor 305. In some cases, the code can be retrieved from the storage unit 315 and stored on the memory 310 for ready access by the processor 305. In some situations, the electronic storage unit 315 can be precluded, and machine-executable instructions are stored on memory 310.

The code can be pre-compiled and configured for use with a machine having a processor adapted to execute the code or can be compiled during runtime. The code can be supplied in a programming language that can be selected to enable the code to execute in a pre-compiled or as-compiled fashion.

Aspects of the systems and methods provided herein, such as the computer system 301, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 301 can include or be in communication with an electronic display 335 that comprises a user interface (UI) 340. Examples of user interfaces (UIs) include, without limitation, a graphical user interface (GUI) and web-based user interface. For example, the computer system can include a web-based dashboard (e.g., a GUI) configured to display, for example, patient metrics, recent notifications, and/or assessments, thereby allowing health care providers, such as physicians and treating teams of a patient, to access patient notifications, data (e.g., sensor data), and/or predictions or assessments generated from such data.

Methods and systems of the present disclosure can be implemented by way of one or more algorithms. An algorithm can be implemented by way of software upon execution by the central processing unit 305. The algorithm can, for example, acquire sensor data comprising a plurality of motor task measurements of a subject over a period of time, store the acquired sensor data in a database, receive sensor data from one or more sensors (e.g., an accelerometer sensor) through a wireless transceiver, and process sensor data using a trained algorithm to generate a clinical assessment of a neurological disease, disorder, or condition in a subject.

EXAMPLES

Example 1—Assessment of Motor Function Using a Mobile Device

Dopaminergic neuronal loss has been associated with poor motor function and can be a biological marker of some neurodegenerative diseases, for example, Parkinson's disease (PD) and rapid eye movement (REM) sleep behavior disorder (RBD). Using methods and systems of the present disclosure, a subject's motor function was quantified. A remotely captured digital motor composite score (MCS) generated through the digital tests performed in less than 10 minutes on a smartphone was an accurate predictor of the result of a Dopamine Active Transporter ioflupane ($^{123}$I) single photon emission computed tomography scan (DaTscan or DaT SPECT scan), an imaging technology that allows visualization of the dopamine system in the brain striatum. Digital Motor Composite Score (MCS) Acquisition and Calculation Protocol Data was collected from participants enrolled in the Oxford Parkinson's disease Centre (OPDC) Discovery study using smartphone assessments at of subjects at a clinic visit and then at home over a maximum of seven days. The seven assessments included measures of voice (FIG. 1A), balance (FIG. 1B), gait (FIG. 1C), finger tapping (FIGS. 1D-1E), reaction time (FIGS. 1F-1G), rest (FIG. 1H), and postural tremor (FIG. 1I). These seven tasks were aimed at quantifying a range of motor impairments associated with Parkinson's disease (PD).

Figure 1A:
FIG. 1A illustrates an example of an application graphical user interface (GUI) for a Voice Exercise task.

For the voice task, using the inbuilt microphone, sustained phonation using an "aaah" sound was recorded (FIG. 2A); the participants were instructed to "Hold the phone to your ear, take a deep breath, and say "aaah" at a comfortable and steady, tone and level, for as long as you can" (FIG. 1A).

For the balance task, using the smartphone inertial measurement units (IMUs), triaxial accelerometer sensor data was collected (FIG. 2B); the participants were instructed to "Stand up straight and place the phone in your pocket. When the buzzer vibrates and auditory alert sounds, stay standing until the buzzer vibrates and the alert sounds again" (FIG. 1B).

For the gait task, using the smartphone IMUs, triaxial accelerometer sensor data was collected (FIG. 2C); the participants were instructed to "Stand up and place the phone in your pocket. When the buzzer vibrates and auditory alert sounds, walk forward 20 yards. Then, stop, turn around, and walk back again" (FIG. 1C).

Figure 1D:
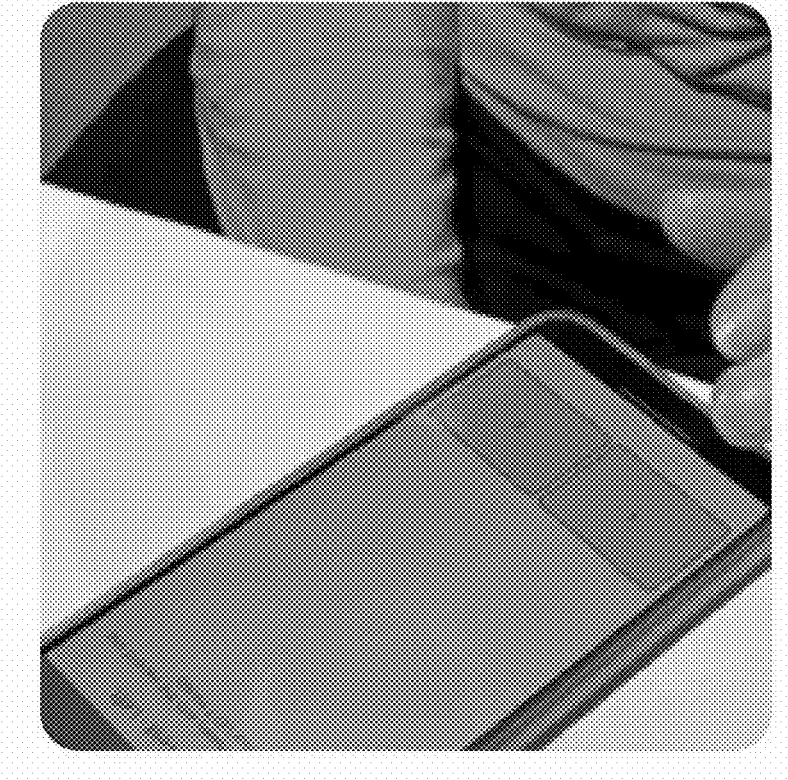
FIGS. 1D-1E illustrate an example of an application GUI for a Finger Tapping Exercise task.
Figure 1E:
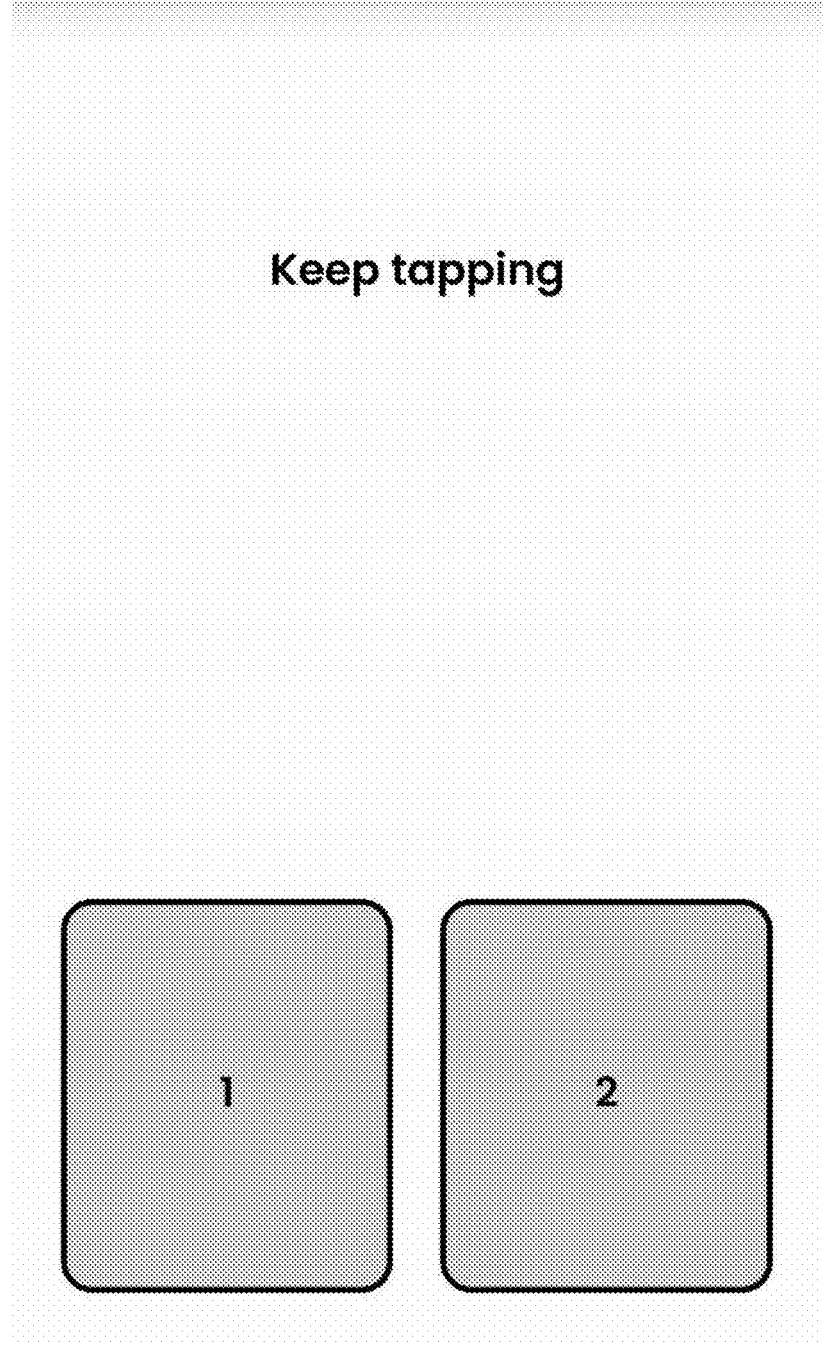

For the finger tapping task, using the touch screen sensors and timer, time and location (x-y screen coordinate position) of finger touch was recorded (FIG. 2D); participants were instructed to "Tap the buttons below with the index and middle fingers of 1 hand alternatively, in a regular rhythm" (FIGS. 1D-1E).

Figure 1G:
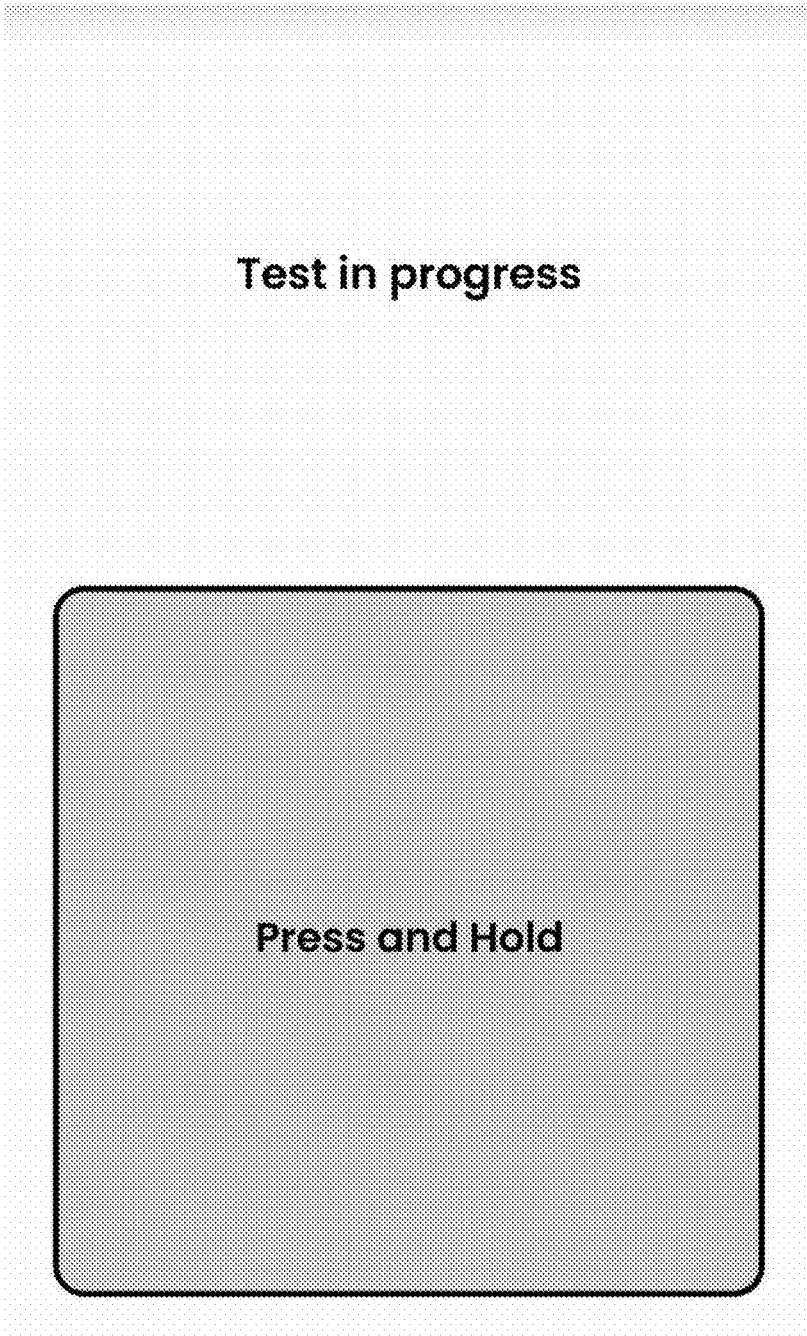

For the reaction time task, using the touch screen sensors and timer, the time of stimulus onset (appearance/disappearance of a screen button) and response (press/release the screen button) along with location (x-y screen coordinate position) of finger touch was recorded (FIG. 2E); participants were instructed to "Press the screen button below as soon as it appears; release as soon as it disappears" (FIGS. 1F-1G).

Figure 1H:
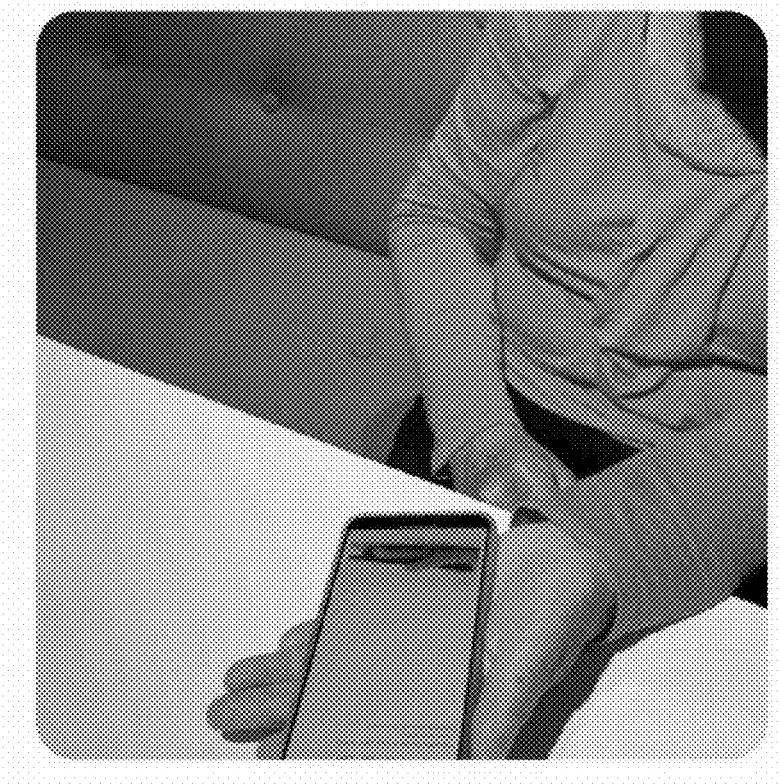
FIG. 1H illustrates an example of an application GUI for a Rest Tremor Exercise task.
Figure 1I:
FIG. 1I illustrates an example of an application GUI for a Postural Tremor task.

For the rest tremor task, using the smartphone IMUs, triaxial accelerometer sensor data was collected (FIG. 2F); participants were instructed to "Sit upright, hold the phone in your left hand and rest it lightly on a hard flat surface, and close your eyes." This was then repeated in the right hand (FIG. 1H).

For the postural tremor task, using the smartphone IMUs, triaxial accelerometer sensor data was collected (FIG. 2G); participants were instructed to "Sit upright and hold the phone in your left hand, with the arm outstretched in front of you." This was then repeated in the right hand (FIG. 1I).

Single features or combinations of features from the individual smartphone tests of voice, balance, gait, finger tapping, reaction time, rest tremor or postural tremor are able to detect changes that correlate clinically with patient symptoms, their responses to medication, and responses to other treatments such as Deep Brain Stimulation Using the data collected during a subject's performance of the seven tasks described above and a digital smartphone motor composite score (MCS) was obtained using a machine learning approach. The machine learning model used to create the digital smartphone motor composite score was exhaustively validated on both an internal dataset: 641 PD, 288 iRBD (prodromal PD) and 46 control participants from the Oxford Discovery cohort, and external data set: 74 PD participants from the Exenatide PD Phase 3 trial using on and off medication assessments.

DaT SPECT/CT Acquisition and Analysis Protocol

The study that gathered the DaTScan and digital motor composite score (MCS) data was approved by the University of Oxford Clinical Trials and Research Governance Department, the local Health Research Authority Research Ethics Committee, and the UK Administration of Radioactive Substances Advisory Committee. Written, informed consent was obtained from all participants.

16 Parkinson's disease (PD), 2 healthy control and 29 rapid eye movement (REM) sleep behavior disorder (RBD) patients from the Oxford Parkinson's disease Centre Discovery cohort performed the digital MCS test in clinic, with DaTScan acquired within a maximum 3 month time interval. All RBD diagnoses were made by polysomnography according to the International Classification of Sleep Disorders criteria.

Dopamine Active Transporter ioflupane ($^{123}$I) single photon emission tomography (DaTscan or DaT SPECT scan) SPECT/CT scans were acquired according to the standard clinical protocol at the Department of Nuclear Medicine, Churchill Hospital, Oxford. Any patients taking antidepressant medication was withheld for at least 24 hours prior to imaging. Potassium iodide 120 mg was administered one hour prior to, and 24 hours after, injection of $^{123}$I-ioflupane to block thyroid uptake. Subjects were injected with 185 MBq+/−10% of $^{123}$I-ioflupane (provided as DaTscan™ injection, GE Healthcare). SPECT/CT images were acquired three hours post injection on a Discovery 670 gamma camera (GE Healthcare, Haifa). SPECT acquisition parameters were as follows: 120 projections, 30 seconds per projection, 128×128 matrix. CT parameters were as follows: 16 slice, helical acquisition, 120 KV, 40 mA, noise index 30. The SPECT/CT data was reconstructed using HERMES Hybrid Recon (HERMES Medical Solutions, AB Stockholm) OSEM, 15 iterations, 4 subsets with attenuation correction from CT, collimator resolution recovery, and Monte Carlo scatter correction. The isotropic voxel size of reconstructed images was 2.21 mm. HERMES Hybrid Recon was used for semi-quantification of DaT_SPECT images. Bilateral specific to non-displaceable binding ratios (SBRs) at putamen and caudate levels were computed using pre-defined regions of interest, using occipital lobe uptake as the background reference region. Striatal SBRs were calculated as the mean of caudate and putamen. SBRs for caudate/putamen/striatum both ipsilateral and contralateral to the worst motoric clinically affected side, determined using Movement Disorders Society-Unified Parkinson's Disease Rating Scale (MDS-UPDRS III scale) ratings were calculated. Digital motor composite scores were also calculated for both sides.

Non-parametric correlations between SBRs and digital motor composite scores were performed to calculate the Spearman correlation coefficient.

Correlation of Digital Motor Composite Score (MCS) with DaTscan Binding Ratio

Methods and systems of the present disclosure used the digital motor composite score (MCS) to generate an accurate individual-level estimate of DaTscan striatal binding ratio for the diagnosis, monitoring, stratification and treatment of people with PD and its earlier prodromal stages, exemplified by participants with REM sleep behavior disorder (RBD). The smartphone digital MCS was used to quantify the severity of motor impairment in PD and RBD and was correlated with DaT binding ratios (Table 1), an imaging marker of degeneration in parts of the brain important for motor function.

The digital MCS correlates strongly with DaTscan dopamine binding ratio for striatum, putamen and caudate ipsilateral (FIG. 4A, FIG. 4B, and FIG. 4C, respectively) and contralateral (FIG. 5A, FIG. 5B, and FIG. 5C, respectively) to a subject's worst motoric clinically affected side. The accuracy of methods and systems of the present disclosure was comparable to DaTscan in differentiating between healthy subjects, and those subjects with RBD and PD.

TABLE 1

Correlation of DaT Binding Ratio and Digital Motor Composite Score

| Brain Area | | Spearman Correlation: Brain Area DaT Binding to Digital MCS | |
| --- | --- | --- | --- |
| | | Coefficient | P-Value |
| Ipsilateral | Striatum | −0.665 | 0.0000005 |
| | Putamen | −0.637 | 0.0000020 |
| | Caudate | −0.646 | 0.0000010 |
| Contralateral | Striatum | −0.627 | 0.0000050 |
| | Putamen | −0.639 | 0.0000017 |
| | Caudate | −0.615 | 0.0000050 |

Correlation of Digital Smartphone MCS with Clinical Assessments

Methods and systems of the present disclosure were reflective of clinical changes in subjects. A clinical assessment of motor function loss, the composite clinical motor score (CMS), was calculated by combining components of (1) the Movement Disorders Society-Unified Parkinson's Disease Rating Scale (MDS-UPDRS) III motor examination score; (2) the Purdue Pegboard Test, where the total score was calculated as the sum of the number of pegs inserted over 30 seconds by (a) the left hand, (b) the right hand and (c) bimanually; and (3) the Timed Up and Go Test, the length of time taken to arise from a chair, walk 3 meters in a straight line, turn and walk and sit back down. The first principal component, the component that captured the largest variance in the data and was obtained by applying principal component analysis (PCA) to the clinical scores was used as the CMS.

Using the data collected during a subject's performance of the digital tasks described above and a digital smartphone motor composite score (MCS) was obtained using a machine learning approach. Using only the 50 most salient smartphone features, the CMS can be estimated with a mean error of 4.8 points using features extracted from one administration of the smartphone test assessment. The smartphone test assessment also significantly correlated with the measures from which the CMS was derived, (1) the Movement Disorder Society-Unified Parkinson's Disease Rating Scale part III (MDS-UPDRS-III) motor examination score (correlation coefficient 0.51), (2) the Purdue Pegboard Test (correlation coefficient −0.45), and (3) the Timed Up and Go Test (correlation coefficient 0.45).

The smartphone digital motor composite score is therefore able to estimate the CMS to a high degree of accuracy, and this digital motor composite score is the same score which significantly correlates with patients DaTscan results (Table 1), demonstrating a relationship with both clinical and imagining measures of patients with PD and RBD.

Example 2—Clinical Application of Assessment of Motor Function Using a Mobile Device Methods and systems of the present disclosure are used to stratify subjects into different degrees of risk of presence of neurodegenerative disease (e.g., PD or RBD), influencing clinical decisions and investigation pathways. For example, methods and systems of the present disclosure are used to acquire evidence of dopamine neuron loss.

For example, methods and systems of the present disclosure are used to:

(1) differentiate patients with an abnormal DaTscan from those with a normal DaTscan (e.g., binary classification of normal vs abnormal);

(2) predict the risk or probability that a patient would have an abnormal DaTscan (e.g., risk range from 0-100);

(3) based on the strong non-linear correlation between the digital motor composite score and the DaTscan binding ratios, predict the DaTscan binding ratio to quantify the severity of abnormality in the brain and display these results in different visualizations.

Methods and systems of the present disclosure are useful for screening and stratification of patients, and may replace the need for a DaTscan by providing sufficient evidence of dopaminergic dysfunction to diagnose PD versus other causes of parkinsonism symptoms, e.g., drug induced symptoms or tremor due to other causes such as essential tremor or otherwise.

Although the description has been described with respect to particular embodiments thereof, these particular embodiments are merely illustrative, and not restrictive. Concepts illustrated in the examples may be applied to other examples and implementations.

While preferred embodiments of the present invention have been shown and described herein, it is obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method of performing a clinical assessment of Parkinson's disease on a subject, comprising:

(i) displaying to a subject, via a user interface of a mobile electronic device, a prompt to perform a motor task, wherein the motor task is a member selected from the group consisting of tasks measuring vocalization, balance, gait, tapping, reaction time, resting tremor, and postural tremor;

(ii) acquiring, by one or more sensors of the mobile electronic device, sensor data of the subject during performance of the motor task by the subject, wherein the one or more sensors comprise each of an accelerometer, a touch screen sensor, a video sensor, an audio sensor, and a gyroscope sensor;

(iii) using one or more programmed computer processors to process the sensor data or features extracted therefrom, using a trained machine-learning algorithm, wherein the processing comprises:

(1) determining a simulated dopamine transporter scan (DaTScan) tracer uptake measurement value based at least in part on the sensor data or features extracted therefrom, and (2) generating an output indicative of a state of Parkinson's disease of the subject, wherein the generated output comprises a prediction of dopamine neuron loss based on the simulated DaTScan tracer uptake measurement value; and (iv) based at least in part on the generated output, performing the clinical assessment of Parkinson's disease on the subject, wherein the clinical assessment comprises a radiological brain imaging test or a polysomnography test.

2. The method of claim 1, wherein (iii) further comprises (a) processing the sensor data to determine motor function scores, and (b) processing the motor function scores to generate the output.

3. The method of claim 1, further comprising providing a treatment to the subject based at least in part on the clinical assessment.

4. The method of claim 1, wherein the sensor data comprise a each of inertial measurement units (IMUs), event times, coordinates of an electronic display, audio recordings, digital images, and video recordings.

5. The method of claim 1, wherein (iii) further comprises processing patient reported outcome measure (PROM) data, medication-specific data, or data from a behavioral test of cognitive function, using the trained machine learning algorithm.

6. The method of claim 5, wherein (iii) further comprises processing at least one of the sensor data, the PROM data, or the data from the behavioral test of cognitive function to determine motor function scores; and processing the motor function scores to generate the output.

7. The method of claim 6, wherein the PROM data comprise quality of life, pain, fatigue, patient function, clinical events, or symptom severity data.

8. The method of claim 5, wherein the medication-specific data comprises medication specific to the treatment of Parkinson's disease.

9. The method of claim 1, wherein the trained machine learning algorithm comprises a machine learning classifier.

10. The method of claim 9, wherein the machine learning classifier is selected from the group consisting of a support vector machine (SVM), a naïve Bayes classification, a random forest, a neural network, a deep neural network (DNN), a recurrent neural network (RNN), a deep RNN, a long short-term memory (LSTM) recurrent neural network (RNN), and a gated recurrent unit (GRU) recurrent neural network (RNN).

11. The method of claim 1, wherein the Parkinson's disease comprises dementia with Lewy bodies, multiple system atrophy, prodromal stage Parkinson's disease, progressive supranuclear palsy (PSP), corticobasal degeneration (CBD), REM Sleep Behavior Disorder (RBD), or Parkinson's dementia.

12. The method of claim 1, wherein the radiological brain imaging test comprises determining dopamine neuron loss in a brain area.

13. The method of claim 12, wherein the brain area comprises basal ganglia, striatum, putamen, or caudate nucleus.

14. The method of claim 1, wherein the radiological brain imaging test comprises a Dopamine Active Transporter tomography scan (DaTscan).

15. The method of claim 1, wherein the clinical assessment comprises the polysomnography test.

16. The method of claim 1, further comprising using the polysomnography test to detect a presence or an absence of rapid eye movement (REM) sleep behavior disorder (RBD) in the subject.

17. The method of claim 1, further comprising using the generated output to classify the subject as having a pre-determined outcome of the clinical assessment or likely to have a pre-determined outcome of the clinical assessment.

18. The method of claim 1, wherein the generated output comprises a predicted risk or likelihood of the subject having a pre-determined outcome of the clinical assessment.

19. The method of claim 1, wherein the generated output comprises a predicted severity of Parkinson's disease in the subject.

20. The method of claim 1, wherein the generated output comprises an indication of whether the subject is likely to benefit from enrollment into a clinical trial.

21. The method of claim 1, wherein the generated output comprises an indication of whether the subject is likely to benefit from initiation or alteration of medications or therapies.

22. The method of claim 1, wherein the generated output provides sufficient evidence to detect Parkinson's disease in the subject.

23. The method of claim 1, wherein the generated output comprises an estimated composite clinical motor score (CMS), an estimated clinical cognitive score (CCS), an estimated Unified Parkinson's Disease Rating Scale (UPDRS) total, or a UPDRS-III score.

24. The method of claim 1, wherein the clinical assessment comprises the radiological brain imaging test.

* * * * *